US012781230B2

(12) United States Patent
Kim et al.

(10) Patent No.: US 12,781,230 B2
(45) Date of Patent: Nov. 3, 2026

(54) DEVELOPMENT AND APPLICATION OF POLYMER-COATED GOLD NANOPARTICLE-APTAMER NANOCONSTRUCT HAVING SENSITIVITY TO REACTIVE OXYGEN SPECIES

(71) Applicant: POSTECH RESEARCH AND BUSINESS DEVELOPMENT FOUNDATION, Pohang-si (KR)

(72) Inventors: Won Jong Kim, Pohang-si (KR); Jin Seong Kim, Pohang-si (KR); Hyeong Mok Park, Hwaseong-si (KR)

(73) Assignee: POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 650 days.

(21) Appl. No.: 18/020,145

(22) PCT Filed: Oct. 5, 2021

(86) PCT No.: PCT/KR2021/013605
§ 371 (c)(1),
(2) Date: Feb. 7, 2023

(87) PCT Pub. No.: WO2022/075693
PCT Pub. Date: Apr. 14, 2022

(65) Prior Publication Data
US 2024/0301431 A1 Sep. 12, 2024

(30) Foreign Application Priority Data
Oct. 7, 2020 (KR) ........................ 10-2020-0129318

(51) Int. Cl.
*C12N 15/115* (2010.01)
*A61K 9/51* (2006.01)
*A61K 47/69* (2017.01)
*A61P 27/02* (2006.01)

(52) U.S. Cl.
CPC ............ *C12N 15/115* (2013.01); *A61K 9/513* (2013.01); *A61K 47/6923* (2017.08); *A61K 47/6929* (2017.08); *A61P 27/02* (2018.01); *C12N 2310/16* (2013.01)

(58) Field of Classification Search
None
See application file for complete search history.

(56) References Cited

U.S. PATENT DOCUMENTS

| | | | | |
|---|---|---|---|---|
| 9,096,856 | B2 * | 8/2015 | Wang | G01N 33/86 |
| 11,236,343 | B2 * | 2/2022 | Kim | A61K 47/6929 |
| 2014/0249202 | A1 * | 9/2014 | Davis | A61K 31/337 514/772.3 |
| 2015/0051347 | A1 * | 2/2015 | Kataoka | A61K 47/60 525/435 |
| 2017/0137389 | A1 * | 5/2017 | Zhang | C07K 14/001 |
| 2021/0292759 | A1 | 9/2021 | Kim et al. | |
| 2021/0355496 | A1 * | 11/2021 | Soh | C12N 15/115 |
| 2021/0371863 | A1 | 12/2021 | Kim et al. | |

FOREIGN PATENT DOCUMENTS

| | | | |
|---|---|---|---|
| CN | 109001165 | 12/2018 | |
| KR | 10-2017-0129463 | 11/2017 | |
| KR | 10-2018-0047734 | 5/2018 | |
| KR | 10-2018-0064585 | 6/2018 | |
| KR | 10-2023839 | 9/2019 | |
| WO | WO-2018084562 A1 * | 5/2018 | C12N 15/115 |

OTHER PUBLICATIONS

Matsumoto et al. Polymer Journals 46, 483-491 (Year: 2014).*
Kim et al. ACS Appl. Matter Interfaces 13, 9390-9401, published Nov. 6, 2020 (Year: 2020).*
Jiang et al. Microcrhim Acta 184:4305-4312 (Year: 2017).*
Kim et al. ACS Appl. Matter Interfaces 13, Supporting Information, pp. 1-12, published Nov. 6, 2020 (Year: 2020).*
Kim et al. Biomaterials 75 102-111 (Year: 2016).*
Cai et al. Nanotechnology, Science and Applications, 17-32 (Year: 2008).*
Eric Dausse et al., "Aptamers: a new class of oligonucleotides in the drug discovery pipeline?" Current Opinion in Pharmacology 9.5 (Aug. 28, 2009): 602-607.
Fadwa Odeh et al., "Aptamers chemistry: Chemical modifications and conjugation strategies" Molecules. 2020, 25, 3 (Dec. 18, 2019).
Jiwon Yeo et al., "Tannic acid-based nanogel as an efficient anti-inflammatory agent" Biomaterials science 8.4 (Oct. 2019): 1148-1159.
Jinseong Kim et al., "Polymer/Aptamer-Integrated Gold Nanoconstruct Suppresses the Inflammatory Process by Scavenging ROS and Capturing Pro-inflammatory Cytokine TNF-α" ACS Applied Materials & Interfaces 13.8 (Nov. 6, 2020): 9390-9401.

* cited by examiner

*Primary Examiner* — Brian Whiteman
(74) *Attorney, Agent, or Firm* — LEX IP MEISTER, PLLC

(57) ABSTRACT

The present disclosure relates to a polymer-coated gold nanoparticle-aptamer nanoconstruct having reactive oxygen species sensitivity and capable of treating inflammatory diseases through reactive oxygen species scavenge and TNF-α capture.

13 Claims, 29 Drawing Sheets

Specification includes a Sequence Listing.

SEQUENCE LISTING

```
<160> NUMBER OF SEQ ID NOS: 3

<210> SEQ ID NO 1
<211> LENGTH: 65
<212> TYPE: DNA
<213> ORGANISM: Artificial Sequence
<220> FEATURE:
<223> OTHER INFORMATION: aptamer

<400> SEQUENCE: 1

acctggggga gtattgcgga ggaaggtttt ttttggtgga tggcgcagtc ggcgacaatt      60

ttttt                                                                 65


<210> SEQ ID NO 2
<211> LENGTH: 66
<212> TYPE: DNA
<213> ORGANISM: Artificial Sequence
<220> FEATURE:
<223> OTHER INFORMATION: fused aptamer (VEGF apatamer and ATP aptamer)

<400> SEQUENCE: 2

acctggggga gtattgcgga ggaaggtttt tttcccgtct tccagacaag agtgcagggt      60

tttttt                                                                66


<210> SEQ ID NO 3
<211> LENGTH: 65
<212> TYPE: DNA
<213> ORGANISM: Artificial Sequence
<220> FEATURE:
<223> OTHER INFORMATION: aptamer
```

-continued

<400> SEQUENCE: 3

```
acctggggga gtattgcgga ggaaggtttt ttttgacttg gtgcagacga tggcagggtt     60

ttttt                                                                 65
```

DEVELOPMENT AND APPLICATION OF POLYMER-COATED GOLD NANOPARTICLE-APTAMER NANOCONSTRUCT HAVING SENSITIVITY TO REACTIVE OXYGEN SPECIES

TECHNICAL FIELD

This application claims the benefit of Korean Patent Application No. 10-2020-0129318 filed on Oct. 7, 2020, with the Korean Intellectual Property Office, the disclosure of which is herein incorporated by reference in its entirety.

The present disclosure relates to development and application of a polymer-coated gold nanoparticle-aptamer nanoconstruct having reactive oxygen species sensitivity, and more specifically, to a that nanoconstruct can capture disease-related factors such as cytokines related to the progression of diseases through an aptamer with which the gold nanoparticle is modified, and that can be utilized in various diseases such as inflammatory diseases through a polymer coating capable of controlling reactive oxygen species whose production is known to increase in inflammatory diseases.

BACKGROUND ART

An aptamer refers to a single-stranded DNA or RNA oligonucleotide having a specific three-dimensional structure capable of binding to a specific target with high affinity and specificity like an antibody. There are various targets for aptamers, such as small molecule compounds, peptides, and proteins. These aptamers have advantages, such as smaller size, better tissue permeability, ease of chemical modification, and no immune response in the body, compared to antibodies.

However, when the aptamer is to be utilized in the body, it has a problem of poor stability in the body, so it is common to develop and utilize a hybrid material such as combining with polyethylene glycol (PEG). In particular, gold nanoparticle-aptamer hybrid materials have been actively studied for diagnostic and therapeutic purposes due to their ease of synthesis and application and high stability.

However, the conventional gold nanoparticle-aptamer hybrid materials do not fully utilize the functionality of the aptamer, and the case of utilizing the target material capturing ability of the aptamer to form a nanoconstruct is largely unknown.

Reactive oxygen species (ROS) and TNF-α are representative inflammatory factors and are known to be overexpressed in inflammatory diseases and the like to exacerbate the diseases, and reactive oxygen species and VEGF are known to be overexpressed in neovascularization-related diseases such as cancer and macular degeneration to exacerbate the diseases. Thus, a therapeutic effect can be obtained by inhibiting TNF-α or VEGF in these diseases, and a TNF-α inhibitor or VEGF inhibitor is actually used for treatment.

In the present disclosure, by extending the functionality of the aptamer, it was attempted to achieve both treatment through target material capture and nanoconstruct formation through target material capture, and a unique nanoconstruct that did not exist before was devised.

The polymer-coated gold nanoparticle-aptamer nanoconstruct of the present disclosure may treat the disease by inhibiting reactive oxygen species through a polymer coating capable of scavenging reactive oxygen species, and inhibiting TNF-α or VEGF through the aptamer.

PRIOR ART DOCUMENTS

Patent Document 1. Korean Patent Publication No. 10-2018-0064585 (ANTIMICROBIAL NANO-COMPLEX AND USES THEREOF)

Patent Document 2. Korean Patent No. 10-2023839 (HIGHLY EFFICIENT APTAMER COMPLEX CONTAINING BRANCHED DNA AND APTAMER, AND USES THEREOF)

DISCLOSURE

Technical Problem

It is an object of the present disclosure to prepare a polymer-coated gold nanoparticle-aptamer nanoconstruct by a simple process and to embody an intelligent nanoconstruct, wherein the polymer coating is removed by scavenging reactive oxygen species only in the presence of reactive oxygen species, and the aptamer captures disease-related factors after the polymer coating is removed.

Technical Solution

In order to achieve the above object, the present disclosure provides the preparation and use of a nanoconstruct consisting of a gold nanoparticle, an aptamer bound to the surface of the gold nanoparticle, and a polymer bound to the aptamer through the central ATP.

The gold nanoparticle may be spherical and may have a size of 10 to 200 nm.

The aptamer is an aptamer in which two types of aptamers exist together in a single strand, wherein one aptamer is an aptamer for binding to a target disease-related factor and may capture the target, and the other aptamer is an aptamer for binding to ATP and interacts with ATP to help form a nanoconstruct.

The target may be a cytokine overexpressed in a specific disease, and may be VEGF or TNF-α.

The polymer is polymerized phenylboronic acid, and may be a copolymer in which phenylboronic acid is bonded to a maleic anhydride polymer, and binds to ATP to form a polymer-coated nanoconstruct.

The polymer may control the binding of the aptamer to the target by scavenging reactive oxygen species.

Advantageous Effects

The present disclosure relates to the preparation and application of a nanoconstruct comprising a gold nanoparticle, an aptamer bound to the surface of the gold nanoparticle, and a polymer bound to the aptamer through the central ATP, and the nanoconstruct may be synthesized by a simple method, the polymerized phenylboronic acid-coated (blocked) aptamer for capturing a target material may be deshielded while reactive oxygen species are effectively removed, and the deshielded aptamer may capture the target material such as TNF-α and VEGF, and thus, it may be utilized as a therapeutic use for diseases such as inflammatory diseases, cancer, and macular degeneration diseases, in which reactive oxygen species, TNF-α, VEGF, and the like are overexpressed.

BEST MODE

Figure 1A:
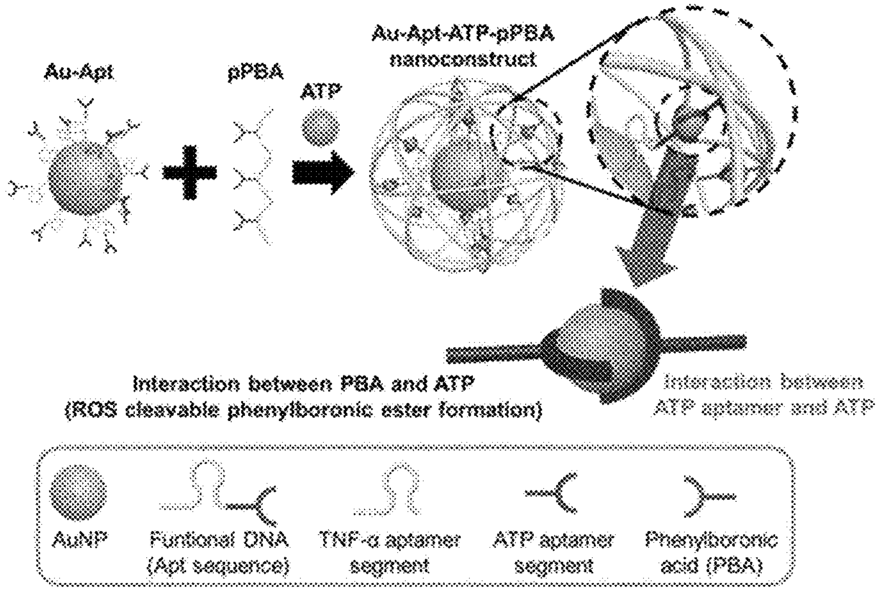
FIGS. 1(*a*) and 1(*b*) is a drawing simulating the formation of the polymer-coated gold nanoparticle-aptamer nanoconstruct according to an embodiment of the present disclosure and its anti-inflammatory action in inflammatory diseases.

Hereinafter, the present disclosure will be described in detail. In the description and drawings of the present disclosure, the description of known content that may obscure the gist of the present disclosure may be omitted, and some of the drawing configuration may be exaggerated or omitted to help understand the present disclosure, and terms not separately defined in the present specification will have to be interpreted as meanings that can be generally understood by those of ordinary skill in the art to which the present disclosure belongs.

In the present specification, an "aptamer" refers to 15-40 single-stranded oligonucleotides that form a specific three-dimensional structure, and has a stem loop structure and a property specifically binding to a specific material based on the three-dimensional structure. The aptamer is easy to chemically synthesize and is a compound that is easy to modify chemically, is stable to heat, and has very high specificity for a target. The sequence of the aptamer may be discovered by the selective evolution of ligands by exponential enrichment (SELEX) method, and hundreds of aptamer sequences have already been disclosed. The aptamer is often compared to an antibody in that it binds to a target molecule with high affinity, but has the advantage of not having an in vivo immune response.

The antibody is a protein molecule and has a relatively large size (~150 kDa), so it is expensive to produce and difficult to modify, whereas the aptamer has the advantage of having a small molecular structure composed of nucleic acids with a length of about 20 to 60 mers and being easy to modify. Since the aptamer consists of nucleic acids, it has very high stability compared to the antibody. Protein or antibody drugs cannot be stored or transported at room temperature, but the aptamer is possible, can maintain its function even after sterilization, and can be regenerated again in a short time even when it is denatured, and thus, it is very easy to apply for diagnostics, which requires long time and repeated use.

However, the aptamer has disadvantages in that it is small in size and has low stability in the body due to the presence of various types of nucleases in serum, but it is possible to reduce the rapid disappearance of the aptamer in the blood by conjugating the aptamer to a polymer such as polyethylene glycol (PEG), or diacylglycerol or cholesterol. In addition, it may be used in the biosensor/chip field by binding biotin to a 5'-end or 3'-end of the aptamer and attaching it to a streptavidin support (Dausse E. et al., Aptamers: a new class of oligonucleotides in the drug discovery pipeline?, Curr. Opin. Pharmacol, 2009).

The present disclosure relates to the preparation and application of a polymer-coated gold nanoparticle-aptamer nanoconstruct that may be utilized in various fields such as inflammatory diseases.

The gold nanoparticle is spherical and may have a size of 10 to 100 nm, 10 to 50 nm, or 10 to 20 nm, but the size of the gold nanoparticle is well known to be adjusted according to its synthetic method, so the size of the gold nanoparticle may be changed according to the purpose of use, and thus, the size of the nanoparticle is not limited. The size refers to the diameter of the gold nanoparticle. The size of the gold nanoparticle may be analyzed by methods such as transmission electron microscope or dynamic light scattering analysis.

An aptamer is bound to the gold nanoparticle, wherein the aptamer comprises an aptamer for a disease-related factor to be captured and a DNA aptamer for ATP to be bound to ATP. Thus, the aptamer is generated by fusion of two types of aptamers. That is, the aptamer has a single-stranded DNA sequence capable of simultaneously having two types of aptamers to bind to two types of target molecules.

Figure 1B:
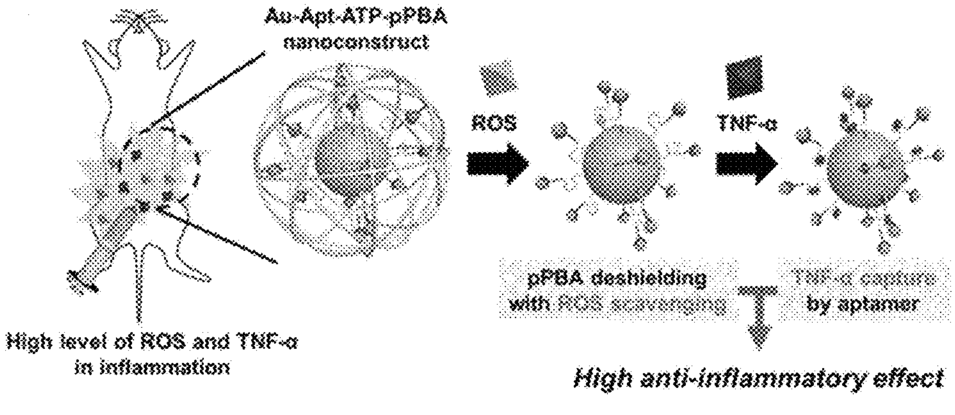

Since ATP has a characteristic of binding to phenylboronic acid, a gold nanoparticle binds to an aptamer for ATP and polymerized phenylboronic acid, which are attached to the gold nanoparticle through ATP as a mediator, so that a polymerized phenylboronic acid cage-coated gold nanoparticle-aptamer nanoconstruct may be formed outside of an aptamer-bound gold nanoparticle, as shown in FIG. 1. Thus, in the preparation of the gold nanoparticle-aptamer nanoconstruct of the present disclosure, the aptamer for ATP is essential for binding to ATP, but the aptamer for a disease-related factor is the aptamer for TNF-α or VEGF shown as an example in the present disclosure and may be changed without limitation depending on the use, as long as it is an aptamer capable of capturing a specific target material.

The disease-related factor may be a biomarker known to be increased in expression according to a disease. Specifically, it may be, but is not limited to, one selected from the cytokines IL-6, TNF-α, IL-1β, MCP-1, and MIP-1α, which are known to be increased in expression by an inflammatory response.

In addition, the disease-related factor may be VEGF. VEGF is an angiogenic factor, and when the expression of VEGF increases, abnormal angiogenesis increases. Specifically, overexpression of VEGF may be observed in diseases such as cancer and macular degeneration.

In addition, the disease-related factor may be thrombin. Thrombin is a factor directly involved in blood clotting, and is involved in thrombus formation and vasoconstriction. Specifically, overexpression of thrombin may be observed in blood clotting-related diseases.

In an embodiment of the present disclosure, the aptamer binding to the gold nanoparticle is a fused form of an aptamer for TNF-α and an aptamer for ATP (SEQ ID NO: 1: ACCTGGGGGAGTATTGCGGAGGAAGGTTTTTTTTGGTGGATGGCGCAGTCGGCGACAATTTT TTT). In addition, in an embodiment of the present disclosure, a fused form of an aptamer for VEGF and an aptamer for ATP (SEQ ID NO: 2: ACCTGGGGGAGTATTGCGGAGGAAGGTTTTTTTCCCGTCTTCCAGACAAGAGTGCAGGGTTT TTTT-Thiol) may be used. The 3'-end of the aptamer is modified with a thiol (—SH) group for binding to the gold nanoparticle.

The gold nanoparticle-aptamer of the present disclosure binds to polymerized phenylboronic acid [poly(methylvinyl ether-maleic anhydride)], which is a phenylboronic acid-bound maleic anhydride polymer, through ATP as a mediator, to finally produce a polymerized phenylboronic acid-coated gold nanoparticle-aptamer nanoconstruct. The polymerized phenylboronic acid may be used without limitation as long as it is a water-soluble polymer containing a plurality of phenylboronic acid.

The ratio of phenylboronic acid in the polymerized phenylboronic acid may be appropriately controlled by adjusting the amount of 3-aminophenylboronic acid, which is a phenylboronic acid monomer. The content of phenylboronic acid in the polymerized phenylboronic acid [poly(methylvinyl ether-maleic anhydride)] prepared in the present disclosure is 28%.

Phenylboronic acid may easily bind to the diol of ATP, and the phenylboron ester bond, which is formed at this time, has a property of being sensitively separated by reactive oxygen species, so that the nanoconstruct of the present disclosure may have reactive oxygen species sensitivity and reactive oxygen species scavenging capacity.

That is, the polymerized phenylboronic acid coated in cage form on the gold nanoparticle through ATP as a mediator blocks the aptamer for a disease-related factor, so the disease-related factor does not bind to the aptamer in the normal state, but when the concentration of reactive oxygen species is high, phenylboronic acid scavenges reactive oxygen species, so the aptamer for the disease-related factor is deshielded, and the aptamer captures the desired disease-related factor.

Thus, the nanoconstruct of the present disclosure has a dual function in that it is targeted to a lesion site with a high concentration of reactive oxygen species in the body to scavenge reactive oxygen species and then capture the cytokine and the like, which are overexpressed in the lesion, depending on the type of aptamer.

Reactive oxygen species are oxygen free radicals produced due to the chemical properties of oxygen and oxygen compounds derived therefrom, and collectively include superoxide anion ($O_2^{-}\cdot$), hydrogen peroxide ($H_2O_2$), hydroxyl group (OH·), alkoxyl group (RO·), peroxyl group (ROO·), and the like.

These reactive oxygen species are chemically very unstable and highly reactive, and thus, they cause extensive oxidative damage to enzyme-catalyzed reactions, activation of transcription factors and biomolecules, cells, tissues, and the like in vivo to induce inflammation around them and are involved as a major factor in tissue fibrosis. This oxidative damage causes various diseases in all tissues of the human body. Specifically, it is known to be involved in the development of cancer and the progression of the developed cancer in various tissues such as skin and kidney, and is known to play an important role in almost all diseases such as cardiovascular disease, inflammation, fibrosis disease, and diabetes.

It was confirmed that the nanoconstruct according to an embodiment of the present disclosure may be prepared without a complicated synthetic process and has reactive oxygen species sensitivity, reactive oxygen species scavenging capacity, and TNF-α capturing ability, and it was confirmed that it did not show cytotoxicity and hematological toxicity and showed high therapeutic effect in cellular and mouse inflammation models. Thus, the nanoconstruct of the present disclosure may be utilized as an anti-inflammatory therapeutic agent.

According to an embodiment of the present disclosure, the inflammatory disease may be, but is not limited to, any one or more selected from the group consisting of pancreatitis, chronic hepatitis, esophagitis, gastritis, colitis, pneumonia, bronchitis, pharyngitis, peritonitis, myocardial infarction, heart failure, Alzheimer's disease, arthritis, renal failure, psoriasis, anemia, diabetes, and fibrosis.

According to an embodiment of the present disclosure, the arthritis may be, but is not limited to, any one or more selected from the group consisting of osteoarthritis, degenerative arthritis, inflammatory arthritis, rheumatoid arthritis, osteochondritis dissecans, joint ligament injury, meniscus injury, joint misalignment, avascular necrosis, and juvenile idiopathic arthritis.

In addition, the nanoconstruct according to an embodiment of the present disclosure has VEGF capturing ability, and thus, it may be used as a therapeutic agent for diseases related to VEGF overexpression, specifically, diseases such as various cancer diseases, rheumatoid arthritis, diabetic retinopathy, ischemic retinopathy, psoriasis, proliferative diabetic retinopathy, and macular degeneration.

In an embodiment of the present disclosure, the efficacy of the nanoconstruct was verified through an inflammation model, but considering the anti-inflammatory principle of the nanoconstruct, it may also be expected to show efficacy in various diseases related to inflammation and may show efficacy against the target disease by changing the aptamer for the disease-related factor, which is a modifiable component.

In the present disclosure, a "therapeutic agent" refers to a composition to be administered for a specific purpose. For the purpose of the present disclosure, the therapeutic agent of the present disclosure is intended to be used for the treatment of cancer, inflammation, or macular degeneration, is a composition comprising a gold nanoparticle-aptamer nanoconstruct as an active ingredient, and may comprise a protein involved therein and a pharmaceutically acceptable carrier, excipient, or diluent.

The "pharmaceutically acceptable" carrier or excipient refers to one approved by a government regulatory department, or one listed in a governmental or other generally approved pharmacopeia for use in vertebral animals, and more particularly in humans.

For parenteral administration, the pharmaceutical composition of the present disclosure may be in the form of a suspension, solution or emulsion in an oily or aqueous carrier, and may be prepared in the form of a solid or semi-solid. In addition, the pharmaceutical composition of the present disclosure may comprise formulating agents such as a suspending agent, a stabilizer, a solubilizing agent, and/or a dispersing agent, and may be sterilized. The pharmaceutical composition may be stable under the conditions of manufacture and storage, and may be preserved against the contaminating action of microorganisms such as bacteria and fungi. Alternatively, the pharmaceutical composition of the present disclosure may be in sterile powder form for reconstitution with an appropriate carrier prior to use. The pharmaceutical composition may be present in unit-dose form, in a microneedle patch, in an ampoule or in other unit-dose container, or in a multi-dose container. Alternatively, the pharmaceutical composition may be stored in a freeze-dried (lyophilized) state requiring only the addition of a sterile liquid carrier, for example, water for injection immediately prior to use. An immediately injectable solution and suspension may be prepared as a sterile powder, a granule, or a tablet.

In some non-limiting embodiments, the pharmaceutical composition of the present disclosure may be formulated, or contained in a liquid in the form of microspheres. In certain non-limiting embodiments, the pharmaceutical composition of the present disclosure may comprise pharmaceutically acceptable compounds and/or mixture thereof at a concentration between 0.001 and 100,000 U/kg. In addition, in certain non-limiting embodiments, the excipient that is suitable for the pharmaceutical composition of the present disclosure may include a preservative, a suspending agent, an additional stabilizer, a dye, a buffering agent, an antibacterial agent, an antifungal agent, and an isotonic agent, for example, sucrose or sodium chloride. As used herein, the term "stabilizer" refers to a compound that is selectively used in the pharmaceutical composition of the present disclosure to increase shelf life. In non-limiting implementations, the stabilizer may be a sugar, an amino acid, or a polymer. In addition, the pharmaceutical composition of the present disclosure may comprise one or more pharmaceutically acceptable carriers, wherein the carrier may be a solvent or a dispersion medium. Non-limiting examples of the pharmaceutically acceptable carrier include water, saline solution, ethanol, polyols (for example, glycerol, propylene glycol, and liquid polyethylene glycol), oils, and appropriate mixtures thereof. Non-limiting examples of sterilization techniques that are applied to the pharmaceutical composition of the present disclosure include filtration through a bacteriostatic filter, a combination of sterile agents, irradiation, irradiation with sterile gas, heating, vacuum drying, and freeze drying.

In the present specification, "administration" refers to introducing the composition of the present disclosure into a patient by any appropriate method, and the composition of the present disclosure may be administered through any general route, as long as it can reach a desired tissue. Oral administration, intraperitoneal administration, intravenous administration, intramuscular administration, subcutaneous administration, intranasal administration, intrarectal administration, or intrathecal administration may be made, and for the purpose of the present disclosure, it is preferably administered in the form of an injection, but is not limited thereto.

The treatment method of the present disclosure may comprise administering a pharmaceutically effective amount of the pharmaceutical composition. In the present disclosure, the effective amount may be regulated depending on various factors, including the kind of disease, the severity of the disease, the kind and content of excipients, the kind of formulation and the patient's age, body weight, general health condition, sex and diet, the time of administration, the route of administration, the duration of treatment, and concomitant drugs.

Hereinafter, examples for carrying present disclosure will be described in detail, the following examples correspond to preferred examples for carrying out the present disclosure, and the present disclosure is not limited by the examples.

MODE FOR INVENTION

Example 1. Preparation and Physicochemical Analysis of Polymer-Coated Gold Nanoparticle-Aptamer Nanoconstructs

Figure 2A:
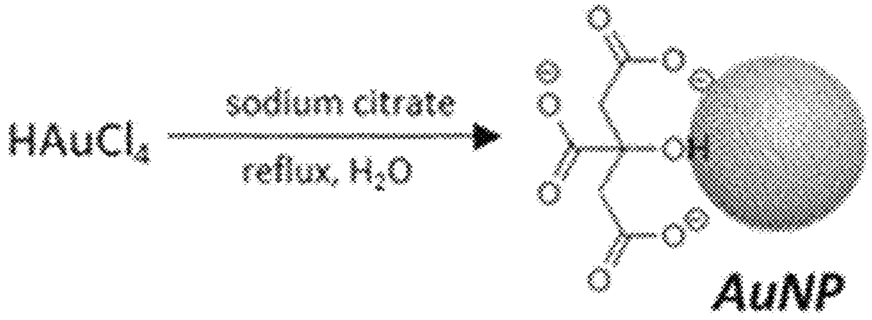
FIGS. 2(*a*) and 2(*b*) is a drawing showing the method for synthesizing a gold nanoparticle according to an embodiment of the present disclosure and the result of transmission electron microscope (TEM) analysis thereof.
Figure 2B:
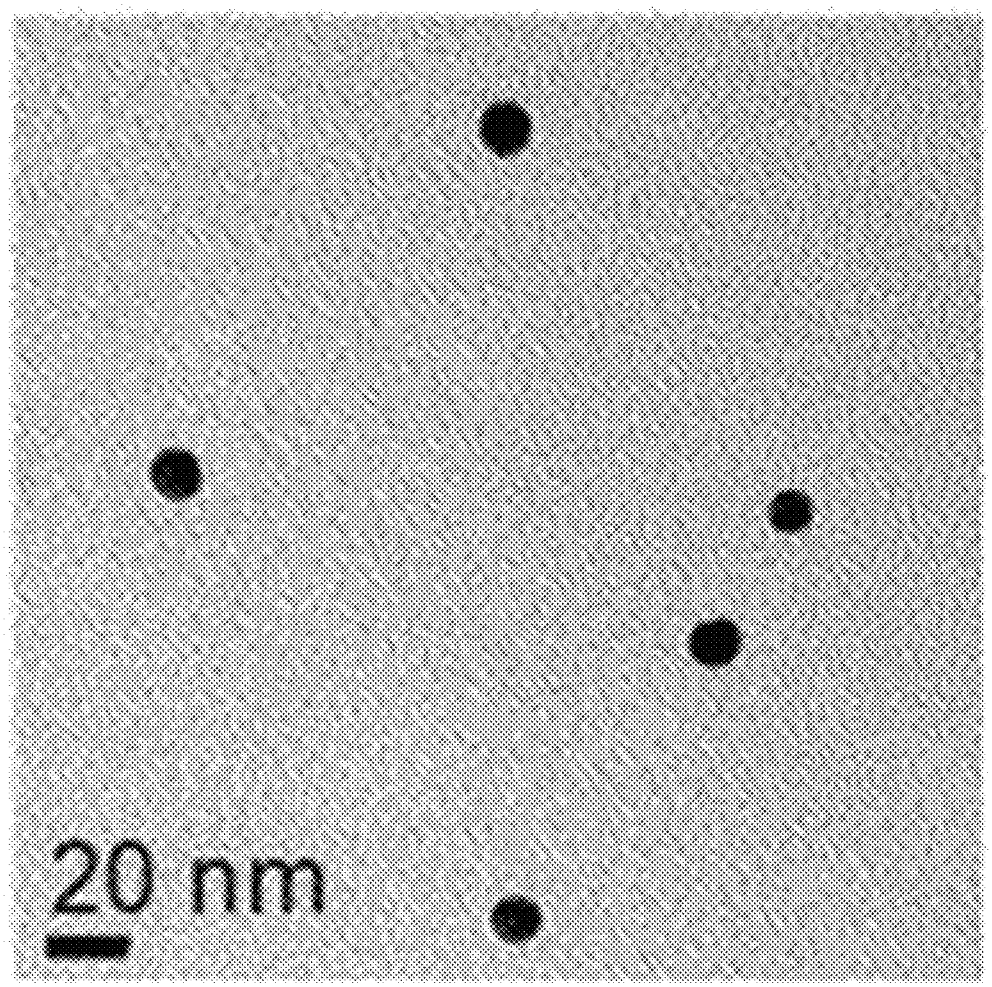
Figure 3A:
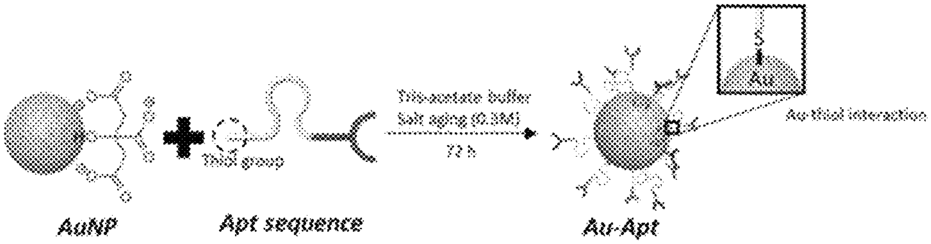
FIG. 3(*a*) through 3(*d*) is a drawing showing the method for synthesizing an aptamer-modified gold nanoparticle according to an embodiment of the present disclosure, the result of dynamic light scattering (DLS) analysis thereof, and the number of aptamers with which the gold nanoparticle is modified.
Figure 3B:
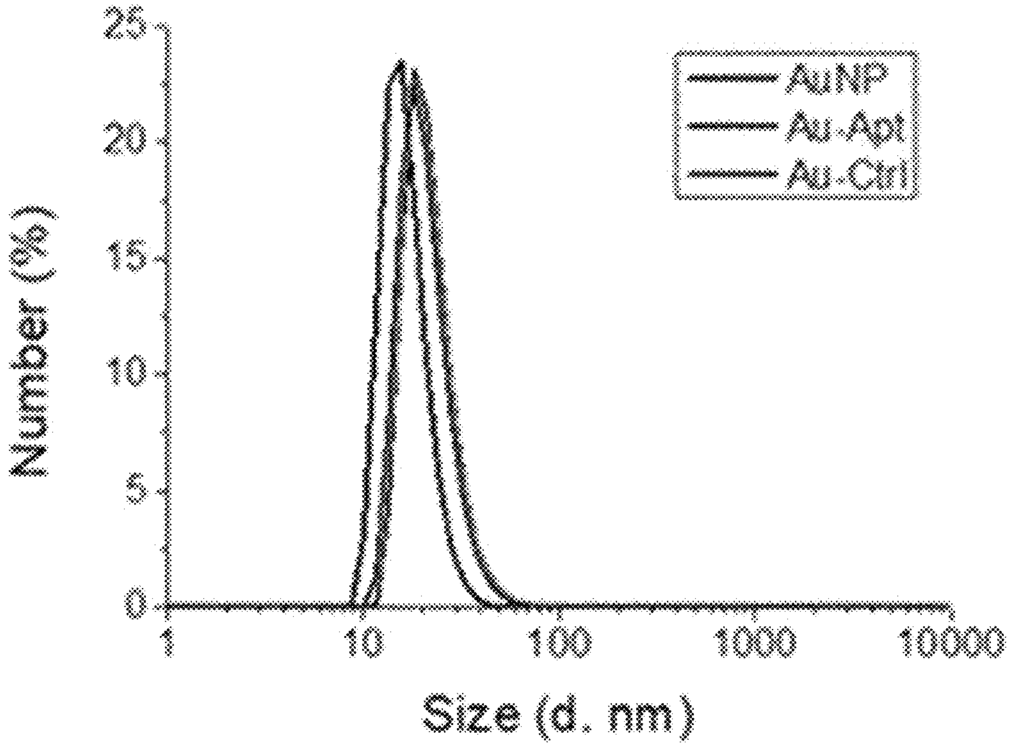
Figure 3C:
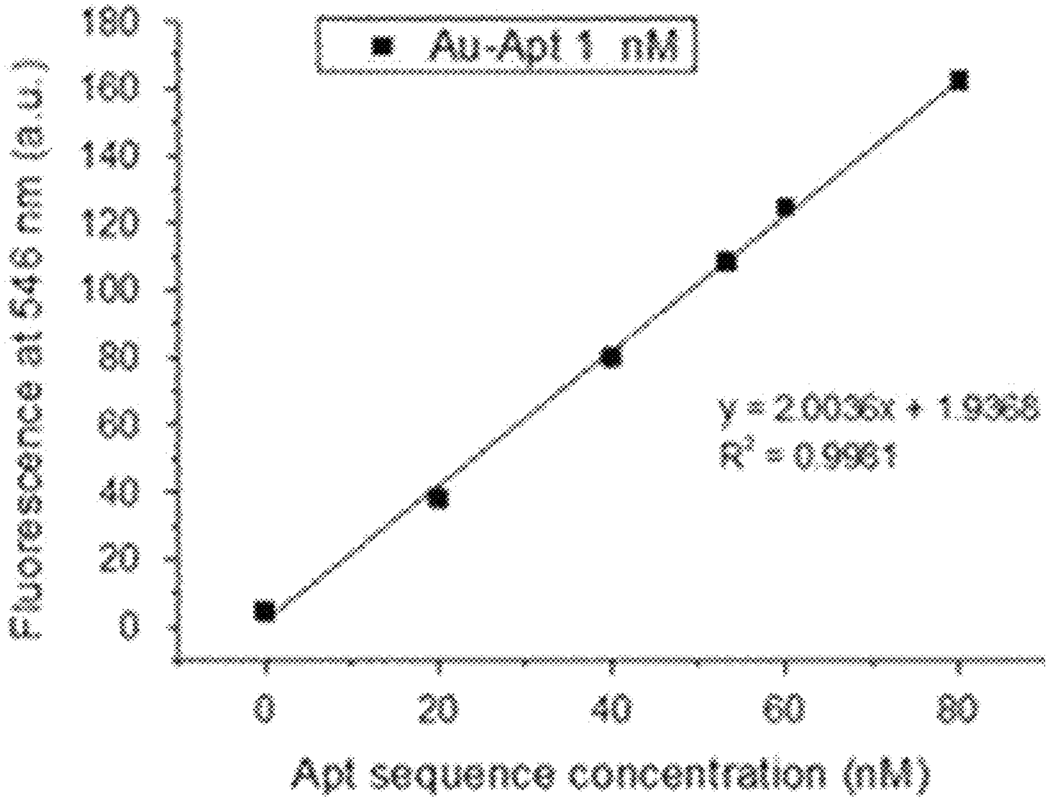
Figure 3D:
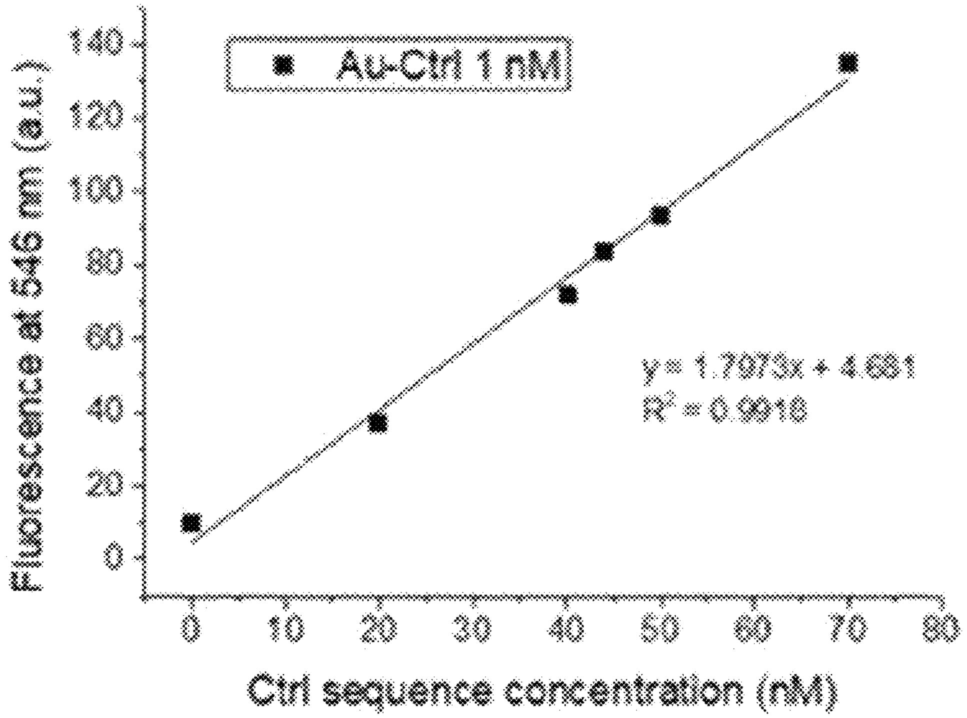

Example 1-1. Preparation of Polymer-Coated Gold Nanoparticle-Aptamer Nanoconstructs Gold nanoparticles were synthesized by preparing 20 ml of 1.47 mM gold chloride hydrate dissolved in distilled water at 100° C., adding 400 μl of 0.34 M sodium citrate thereto, and reacting for 15 minutes. Gold nanoparticles having a size of about 15 nm were confirmed by transmission electron microscopy (FIG. 2).

There were two types of aptamers for binding to a gold nanoparticle to modify the gold nanoparticle, and their specific sequences were described in Table 1 below (SEQ ID NO: 1 and SEQ ID NO: 3). Each aptamer was modified with a thiol (—SH) group at the 3'-end to bind to the gold nanoparticle.

TABLE 1

| Name and sequence number | Base sequence of aptamer used in the present disclosure (5'-3') |
|---|---|
| Apt (SEQ ID NO: 1) | ACCTGGGGGAGTATTGCGGAGGAAGGTTTTTTT TGGTGGATGGCGCAGTCGGCGACAATTTTTT T-Thiol |
| Ctrl (SEQ ID NO: 3) | ACCTGGGGGAGTATTGCGGAGGAAGGTTTTTTT TGACTTGGTGCAGACGATGGCAGGGTTTTTT T-Thiol |

The base sequence of Apt was a sequence including an aptamer for ATP and an aptamer for TNF-α, and the base sequence of Ctrl included only an aptamer for ATP and did not include an aptamer for TNF-α, but was a non-specific sequence for TNF-α having the same length as the Apt sequence.

In order to modify a aptamer to a gold nanoparticle, each aptamer sequence (25 nmol) was activated by reduction with 250 nmol tris(2-carboxyethyl) phosphine hydrochloride (TCEP·HCl), and then added to 5 ml of the previously prepared 15 nM gold nanoparticles and mixed for 52 hours. During mixing, 5 M NaCl was added a total of 3 times at an interval of 4 hours after 16 hours to increase the NaCl concentration in the solution by 0.1 M, and finally to 0.3 M. After synthesis, unreacted materials were removed by centrifugation 3 times at 4,000 rpm for 5 minutes using a 100 kDa Amicon tube.

As shown in the schematic diagram of FIG. 3 (*a*), the thiol group of the aptamer binds to the gold nanoparticles to modify the gold nanoparticles, and the modified gold nanoparticles were named Au-Apt (aptamer for binding to TNF+aptamer for binding to ATP), Au-Ctrl (aptamer for binding to TNF+non-specific aptamer) according to the aptamer sequence.

Figure 4A:
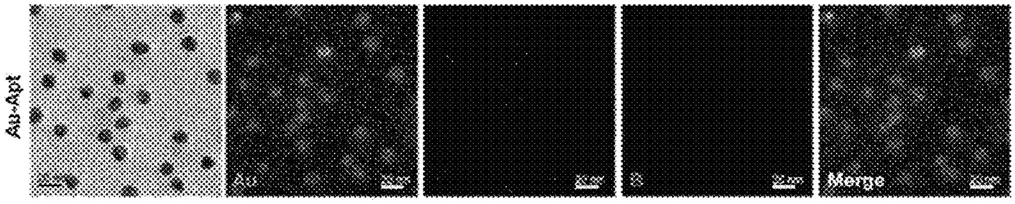
FIGS. 4(*a*) and 4(*b*) is a drawing showing the results of transmission electron microscope analysis and electron energy loss spectrometry analysis of Au-Apt and Au-Ctrl.
Figure 4B:
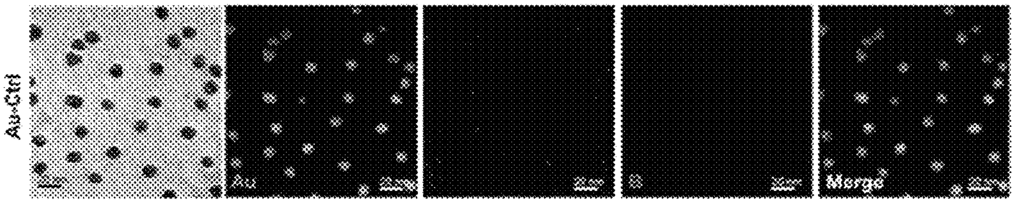

As a result of analyzing each of Au-Apt and Au-Ctrl by dynamic light scattering, it was confirmed that the size was about 20 nm (FIG. 3(*b*)). In addition, as a result of quantifying the amount of DNA by SYBR Gold fluorescence staining after dissolving only gold nanoparticles in 1 nM of each of Au-Apt and Au-Ctrl using 50 mM potassium cyanide in order to calculate the number of aptamers per modified gold nanoparticle, it was confirmed that each of Au-Apt and Au-Ctrl was modified with 53 and 44 aptamers per gold nanoparticle (FIGS. 3(*c*) and 3(*d*)). In addition, the shape of gold nanoparticles and the presence of constituent elements (Au, P) were confirmed through transmission electron microscope analysis and electron energy loss spectrometry analysis (FIG. 4).

Figure 5A:
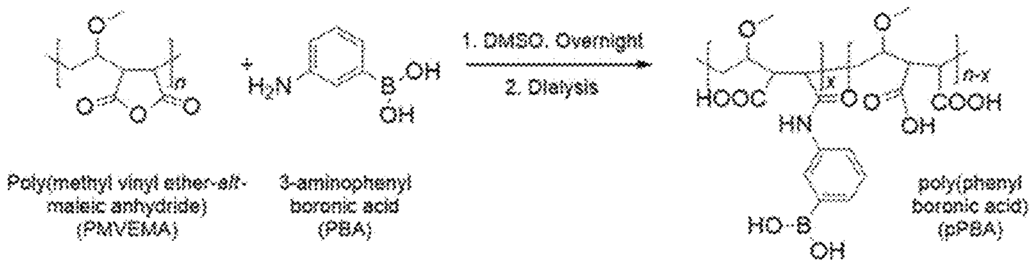
FIGS. 5(*a*) and 5(*b*) is a drawing showing the method for synthesizing polymerized phenylboronic acid according to an embodiment of the present disclosure and the result of H nuclear magnetic resonance analysis thereof.
Figure 5B:
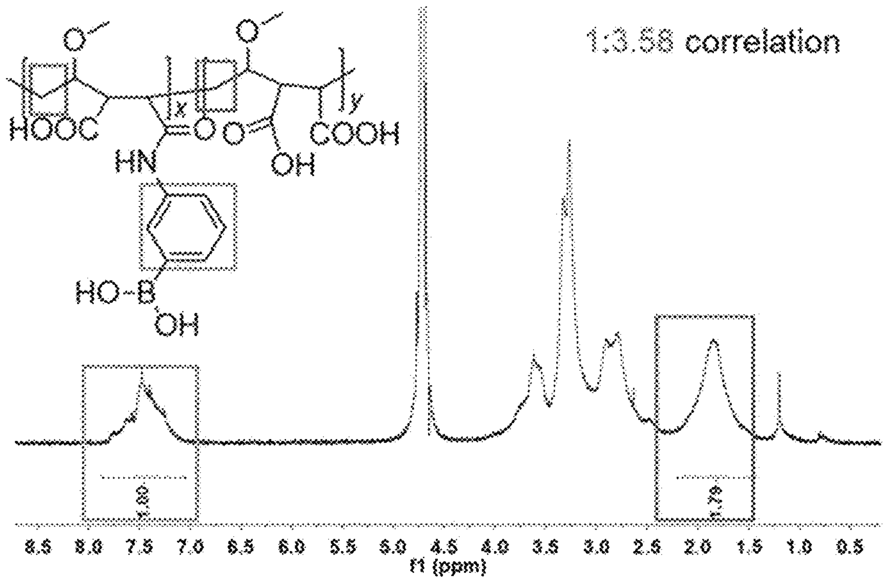

In order to synthesize polymerized phenylboronic acid (poly(phenyl boronic acid); pPBA), poly(methyl vinyl ether-alt-maleic anhydride) (PMVEMA) with a molecular weight of 80 kDa was dissolved in DMSO, and then 3-aminophenyl boronic acid was added thereto so that the molar ratio of maleic acid:phenylboronic acid (PBA) was 30%, and the reaction was carried out at room temperature for 24 hours (FIG. 5 (*a*)). After decomposition of the residual anhydride by hydrolysis with 1 N NaOH, the final product (polymerized phenylboronic acid (poly(phenyl boronic acid); pPBA)), which is a phenylboronic acid-bound maleic anhydride polymer, was obtained through dialysis and freeze-drying using a 10 kDa dialysis membrane. As a result of analysis using H nuclear magnetic resonance analysis in order to quantify the amount of PBA in the final product pPBA, a 28% PBA equivalent was confirmed (FIG. 5). In order to analyze the interaction with aptamer-modified gold nanoparticles, pPBA (Cy5.5-pPBA) in which 1% equivalent of Cy5.5-amine relative to maleic anhydride was added was also prepared, and the synthetic process is the same as above.

Figure 6A:
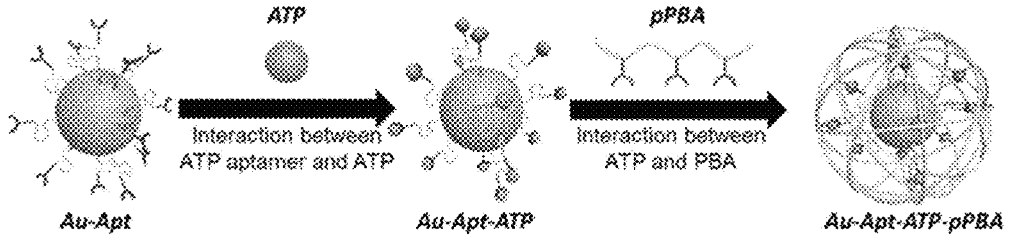
FIG. 6(*a*) through 6(*c*) is a drawing showing the method for synthesizing a polymer-coated gold nanoparticle-aptamer nanoconstruct according to an embodiment of the present disclosure and the result of an aptamer-modified gold nanoparticle-polymer interaction analysis under the presence or absence of ATP.
Figure 6B:
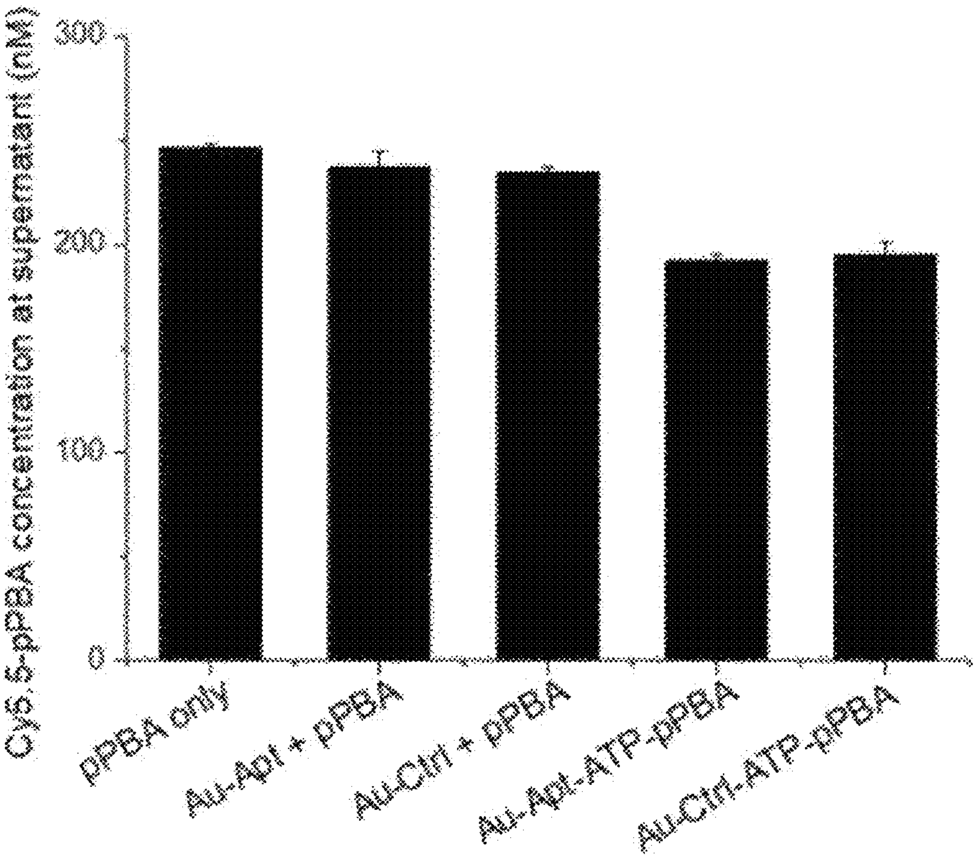
Figure 6C:
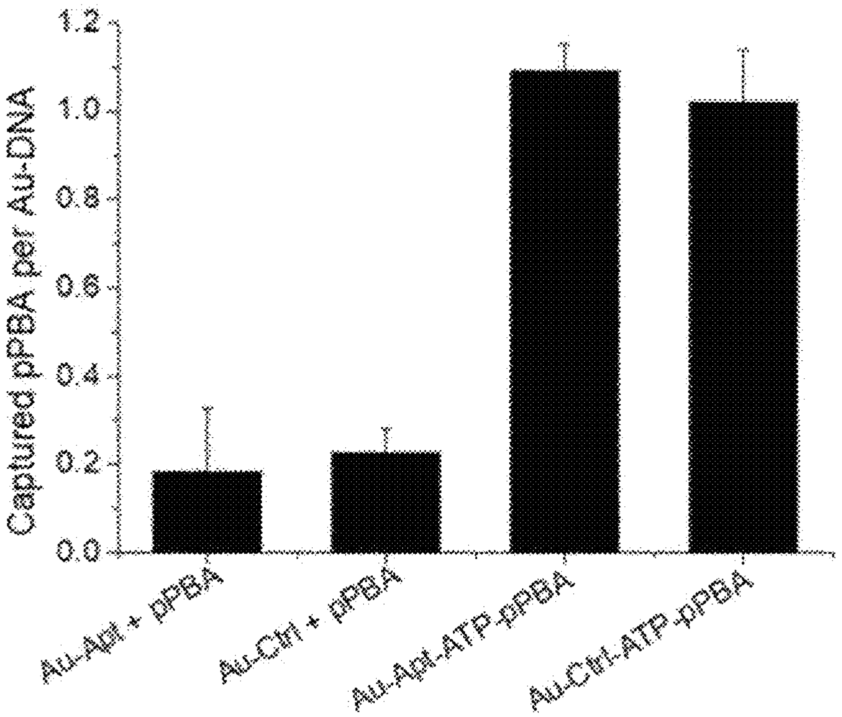

400 nM of Au-Apt or Au-Ctrl and 2 mM ATP were mixed in PBS (pH 8.2) containing 5 mM $Mg^{2+}$ to synthesize pPBA polymer-coated gold nanoparticle-aptamer nanoconstructs, and then the nanoconstructs were obtained by centrifugation at 13,200 rpm for 30 minutes. The obtained material was again dissolved in PBS (pH 8.2) containing 5 mM $Mg^{2+}$, mixed with 2 μM pPBA, and then obtained by centrifugation at 13,200 rpm for 30 minutes. The polymer-coated gold nanoparticle-aptamer nanoconstructs were named Au-Apt-ATP-pPBA and Au-Ctrl-ATP-pPBA according to the aptamer sequence (see FIG. 6 (*a*)). In order to confirm the effect of ATP on the formation of the nanoconstructs, 50 nM of Au-Apt or Au-Ctrl and 250 nM Cy5.5-pPBA were added in PBS (pH 8.2) containing 5 mM $Mg^{2+}$ in the absence of ATP or in the presence of 250 μM ATP. In a next step, as a result of observing the Cy5.5-pPBA fluorescence of the supernatant after centrifugation at 13,200 rpm for 30 minutes, it could be confirmed that the fluorescence decreased only in the presence of ATP, and thus, ATP was significantly involved in the formation of nanoconstructs (FIGS. 6 (*b*) and 6(*c*)).

Figure 7A:
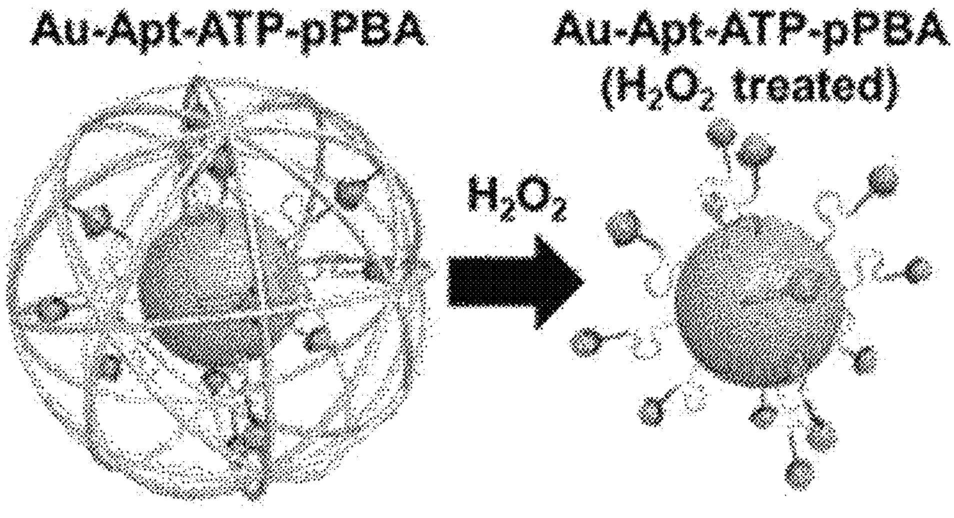
FIGS. 7(*a*) and 7(*b*) is a drawing showing the results of transmission electron microscope analysis and electron energy loss spectroscopy analysis of Au-Apt-ATP-pPBA and Au-Ctrl-ATP-pPBA according to an embodiment of the present disclosure under the presence or absence of reactive oxygen species.
Figure 7B:
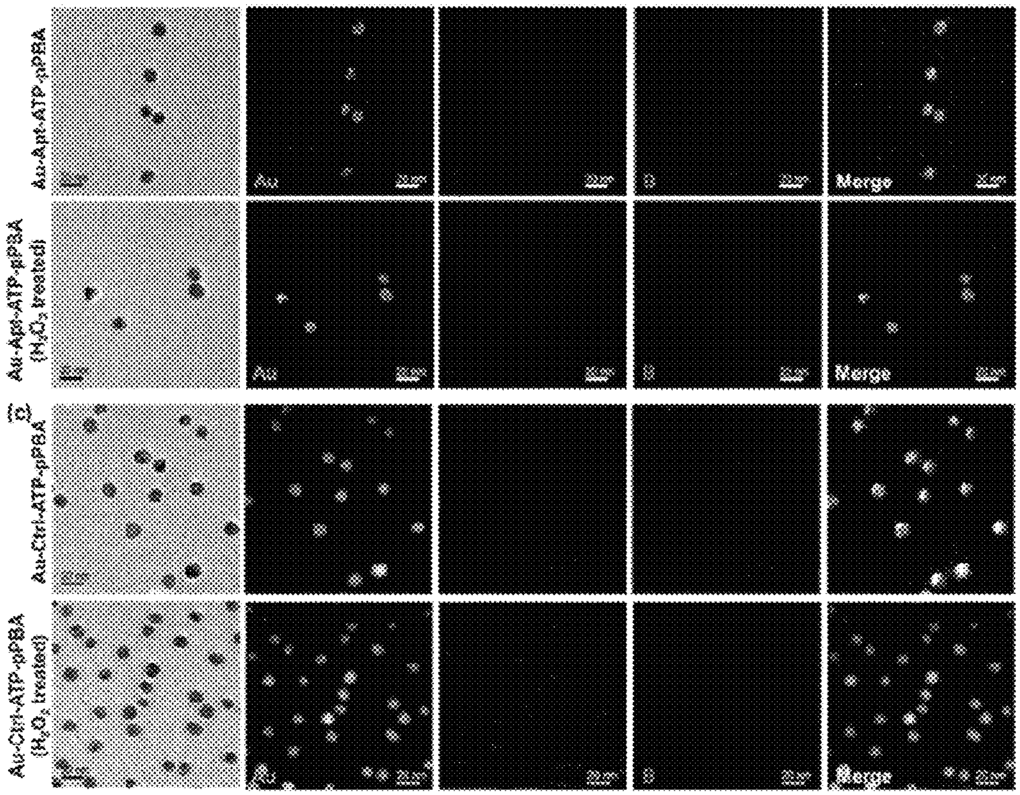

Example 1-2. Confirmation of Reactive Oxygen Species Sensitivity of Polymer-Coated Gold Nanoparticle-Aptamer Nanoconstructs In order to confirm the reactive oxygen species sensitivity of polymer-coated gold nanoparticle-aptamer nanoconstructs (Au-Apt-ATP-pPBA, Au-Ctrl-ATP-pPBA), 40 nM of Au-Apt-ATP-pPBA or Au-Ctrl-ATP-pPBA was mixed with 100 μM hydrogen peroxide ($H_2O_2$) in PBS (pH 8.2) containing 5 mM $Mg^{2+}$, and left at room temperature for 2 hours, and then, transmission electron microscope analysis and electron energy loss spectroscopy analysis (FIG. 7) and dynamic light scattering analysis (FIG. 8) were carried out.

Figure 8A:
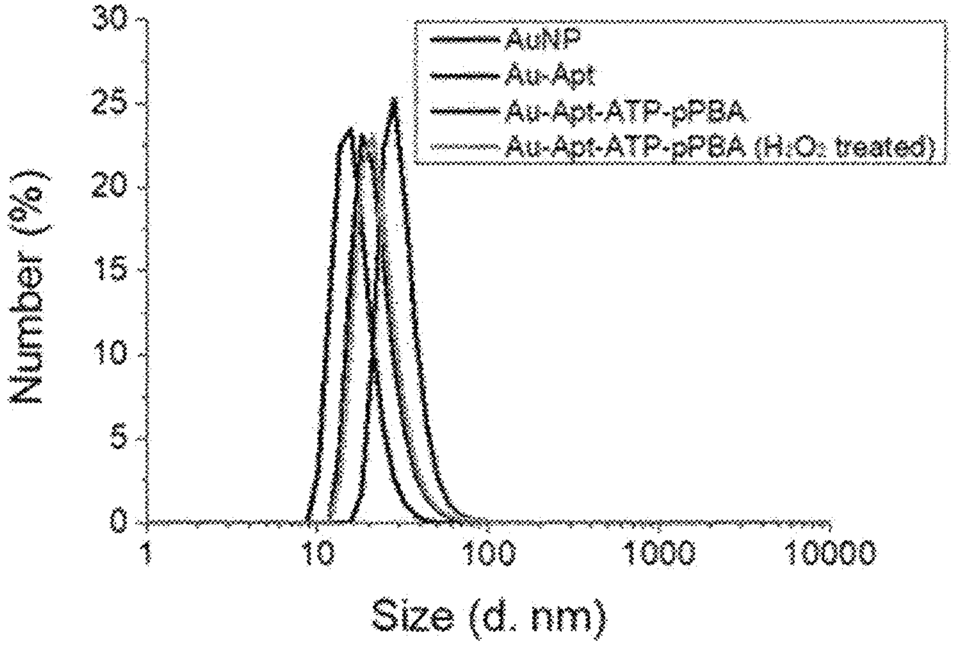
FIGS. 8(*a*) and 8(*b*) is a drawing showing the result of dynamic light scattering analysis of Au-Apt-ATP-pPBA and Au-Ctrl-ATP-pPBA according to an embodiment of the present disclosure under the presence or absence of reactive oxygen species.
Figure 8B:
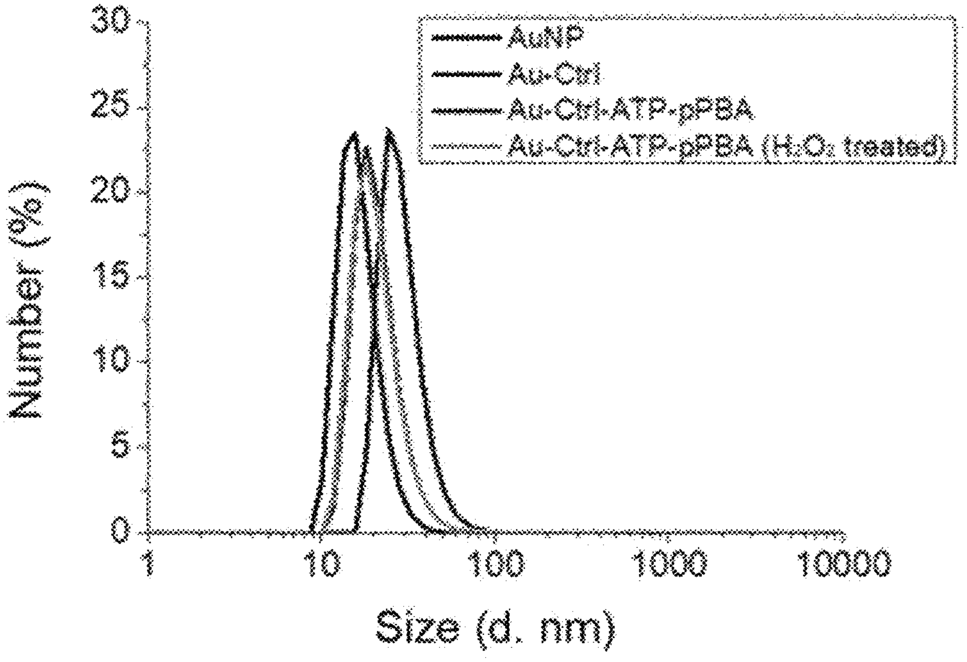

As a result, in the electron energy loss spectroscopy analysis, it could be confirmed that pPBA was removed by reactive oxygen species through the fact that the boron signal of pPBA is detected in the nanoconstructs when there is no reactive oxygen species, but the boron signal of pPBA is not detected when it is sensitive to reactive oxygen species. In addition, in the dynamic light scattering analysis, it could be confirmed that the nanoconstructs of the pPBA were sensitive to reactive oxygen species to remove pPBA through the fact that the sizes of Au-Apt-ATP-pPBA and Au-Ctrl-ATP-pPBA, which were larger than Au-Apt and Au-Ctrl, returned to their original state after sensitization to reactive oxygen species (FIG. 8).

Example 1-3. Confirmation of Reactive Oxygen Species Scavenging Capacity of Polymer-Coated Gold Nanoparticle-Aptamer Nanoconstructs In order to confirm the reactive oxygen species scavenging capacity of polymer-coated gold nanoparticle-aptamer nanoconstructs (Au-Apt-ATP-pPBA, Au-Ctrl-ATP-pPBA), each of 20 nM (based on gold nanoparticles) of Au-Apt, Au-Ctrl, Au-Apt-ATP-pPBA, Au-Ctrl-ATP-pPBA, Au-Apt+pPBA, Au-Ctrl+pPBA, 20 nM pPBA, and 1.15 μM ATP was mixed with 100 μM $H_2O_2$ in PBS (pH 8.2) containing 5 mM $Mg^{2+}$ at room temperature for 2 hours, and centrifuged at 13,200 rpm for 30 minutes, and then, the reactive oxygen species concentration in the supernatant was measured by Amplex Red assay.

Figure 9:
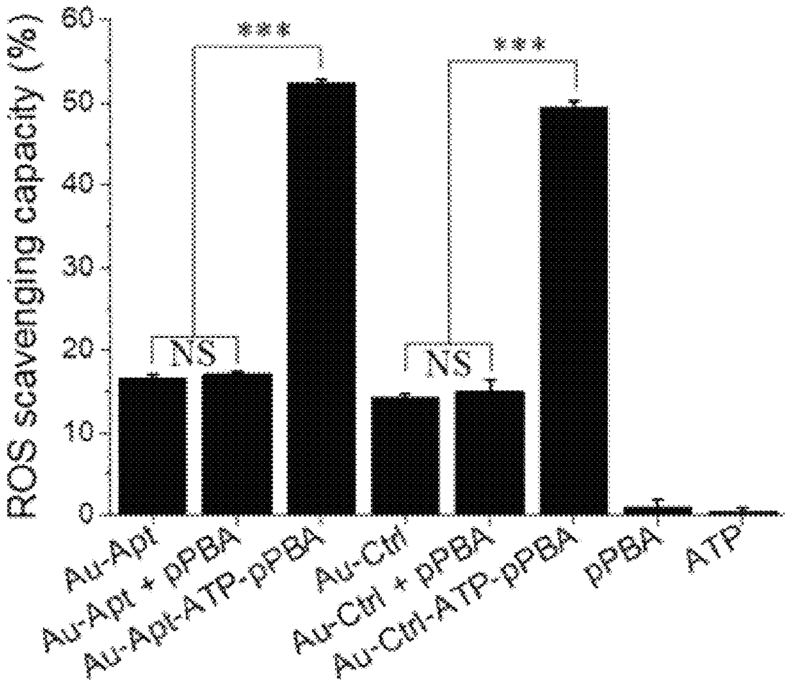
FIG. 9 is a drawing showing the result of evaluating the reactive oxygen species scavenging capacity of various samples comprising Au-Apt-ATP-pPBA according to an embodiment of the present disclosure.

As a result, it could be confirmed that pPBA or ATP did not have reactive oxygen species scavenging capacity, and the reactive oxygen species scavenging capacity did not occur by simply mixing pPBA with Au-Apt or Au-Ctrl without ATP, and only Au-Apt-ATP-pPBA and Au-Ctrl-ATP-pPBA in the form of polymer-coated gold nanoparticles-aptamer nanoconstructs had significantly high reactive oxygen species scavenging capacity (FIG. 9). That is, it could be confirmed once again that Au-Apt-ATP-pPBA and Au-Ctrl-ATP-pPBA were sensitive to reactive oxygen species.

Figure 10A:
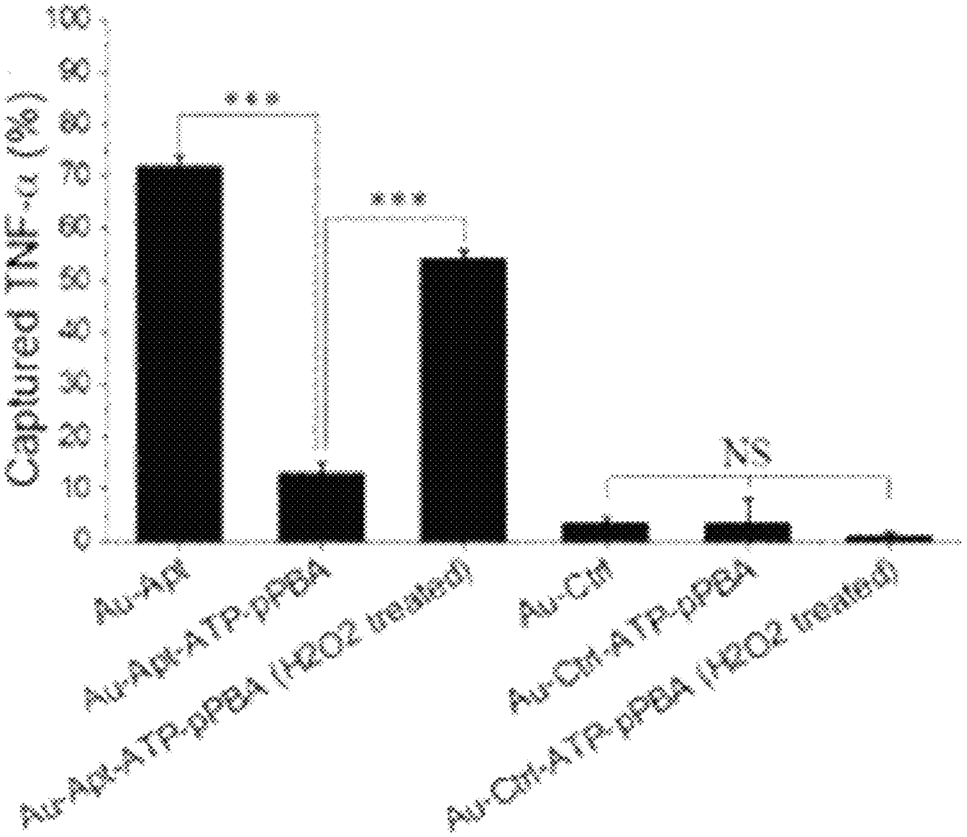
FIGS. 10(*a*) and 10(*b*) is a drawing showing the result of evaluating the TNF-α capturing ability of various samples comprising Au-Apt-ATP-pPBA according to an embodiment of the present disclosure.
Figure 10B:
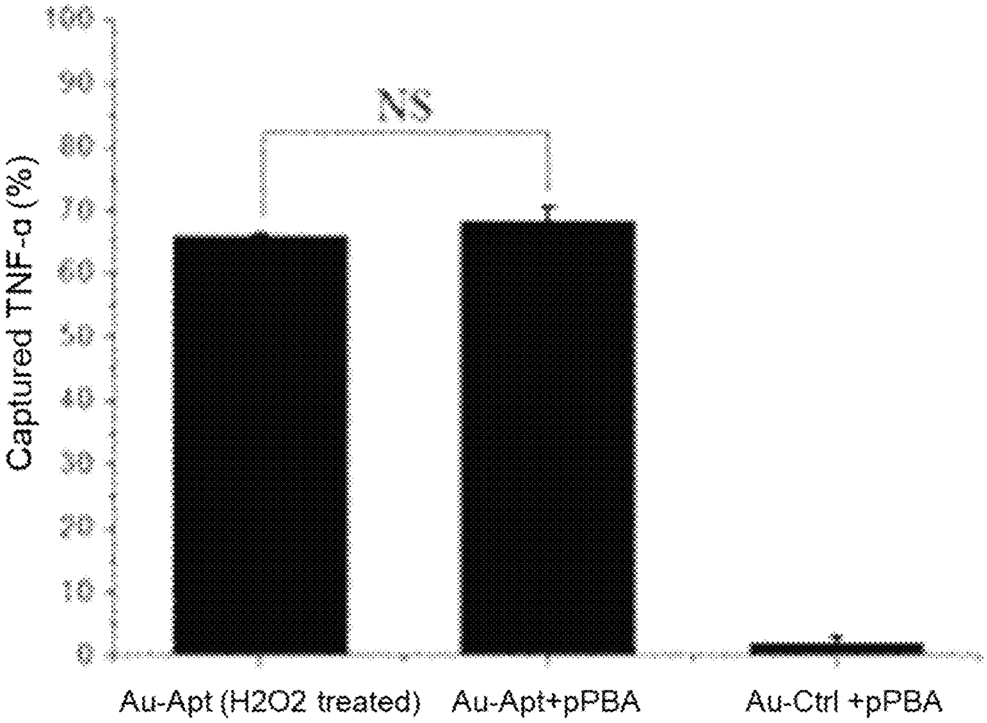

Examples 1-4. Confirmation of TNF-α Capturing Ability of Polymer-Coated Gold Nanoparticle-Aptamer Nanoconstructs In order to confirm the TNF-α capturing ability of polymer-coated gold nanoparticle-aptamer nanoconstructs (Au-Apt-ATP-pPBA, Au-Ctrl-ATP-pPBA), Au-Apt, Au-Ctrl, Au-Apt-ATP-pPBA, Au-Ctrl-ATP-pPBA, Au-Apt+pPBA, Au-Ctrl+pPBA, and 250 pg/mL TNF-α were mixed in PBS (pH 8.2) containing 5 mM $Mg^{2+}$ at an aptamer: TNF-α molar ratio of 10000:1 at 37° C. for 4 hours, and centrifuged at 13,200 rpm for 30 minutes, and then, the TNF-α concentration in the supernatant was measured by enzyme immunoassay. In the $H_2O_2$ treated group, 100 μM $H_2O_2$ was mixed thereto when mixing each component. As a result, Au-Apt-ATP-pPBA showed a remarkably reduced TNF-α capturing ability compared to the aptamer-deshielded Au-Apt because the aptamer for TNF-α was coated (blocked) with pPBA, and shows the TNF-α capturing ability restored upon $H_2O_2$ treatment. This is because pPBA blocking the aptamer was removed by reactive oxygen species of $H_2O$: (FIG. 10 (*a*)). However, it could be confirmed that Au-Apt and Au-Apt+pPBA did not show a reduced TNF-α capturing ability because the aptamer for TNF-α was not blocked with pPBA, and samples such as Au-Ctrl and Au-Ctrl-ATP-pPBA without the aptamer for TNF-α did not capture TNF-α at all regardless of $H_2O_2$ treatment (FIGS. 10(*a*) and 10(*b*)).

From the above, it can be confirmed that Au-Apt-ATP-pPBA may be converted from inactive to active in TNF-α capture according to reactive oxygen species sensitivity.

Example 2. Confirmation of Anti-Inflammatory Effect of Polymer-Coated Gold Nanoparticle-Aptamer Nanoconstructs

Example 2-1. Confirmation of Toxicity of Polymer-Coated Gold Nanoparticle-Aptamer Nanoconstructs Prior to confirming the anti-inflammatory effect of the polymer-coated nanoparticle-aptamer nanoconstructs of the present disclosure, cytotoxicity and hemolysis were analyzed in order to confirm the toxicity of the nanoconstructs itself.

Figure 11:
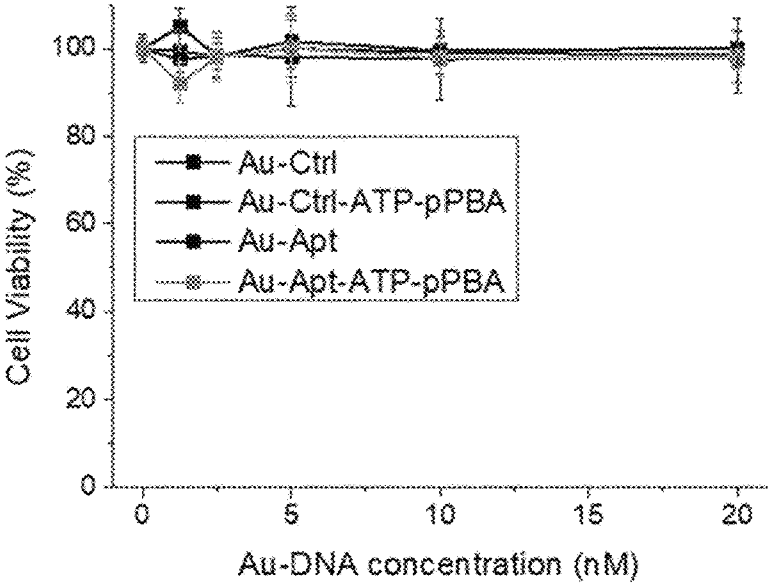
FIG. 11 is a drawing showing the result of evaluating the cytotoxicity of Au-Apt, Au-Ctrl, Au-Apt-ATP-pPBA, and Au-Ctrl-ATP-pPBA according to an embodiment of the present disclosure.

Cytotoxicity was determined by seeding RAW 264.7 cells in a 96-well culture plate at 10,000 cells/well and culturing them for 24 hours, and then replacing the medium, treating them with Au-Apt, Au-Apt-ATP-pPBA, Au-Ctrl, and Au-Ctrl-ATP-pPBA at various concentrations (1.25, 2.5, 5, 10, 20, 40 nM) based on gold nanoparticles, and confirming the viability after 24 hours. As a result, no significant cytotoxicity was observed in all samples used in the experiment (FIG. 11).

Figure 12:
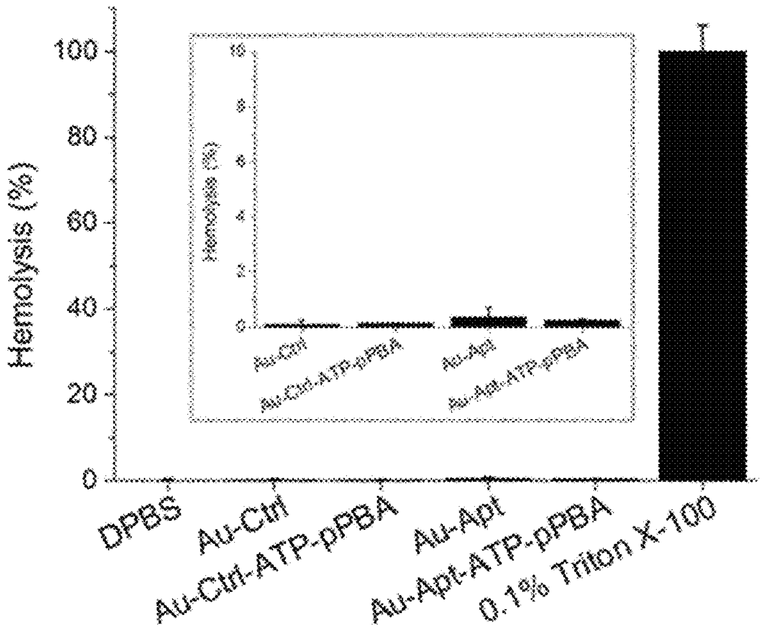
FIG. 12 is a drawing showing the hemolysis test result of Au-Apt, Au-Ctrl, and Au-Apt-ATP-pPBA, and Au-Ctrl-ATP-pPBA according to an embodiment of the present disclosure.

In order to confirm the degree of hemolysis before application to the animal model, red blood cells were isolated after collecting mouse whole blood, and the red blood cell solution was obtained by diluting it 10 times in PBS. Each of 20 nM (based on gold nanoparticles) of Au-Apt, Au-Ctrl, Au-Apt-ATP-pPBA, and Au-Ctrl-ATP-pPBA was mixed thereto for 6 hours, and then centrifuged at 13,200 rpm for 30 minutes, and hemoglobin dissolved in the supernatant was quantified by absorbance at 542 nm. Treatment of the red blood cell solution with PBS was set to 0% hemolysis as a standard, and treatment with a final concentration of 0.1% Triton X-100 was set to 100% hemolysis, and as a result, significant hemolysis was not observed in all nanoconstructs used in the experiment (FIG. 12).

Example 2-2. Confirmation of Intracellular Anti-Inflammatory Effect of Polymer-Coated Gold Nanoparticle-Aptamer Nanoconstructs In order to confirm the intracellular anti-inflammatory effect of polymer-coated gold nanoparticle-aptamer nanoconstructs (Au-Apt-ATP-pPBA, Au-Ctrl-ATP-pPBA), RAW 264.7 cells were activated (inflammation-induced) with phorbol 12-myristate 13-acetate (PMA) or $H_2O_2$, and then the experiment was carried out.

Figure 13A:
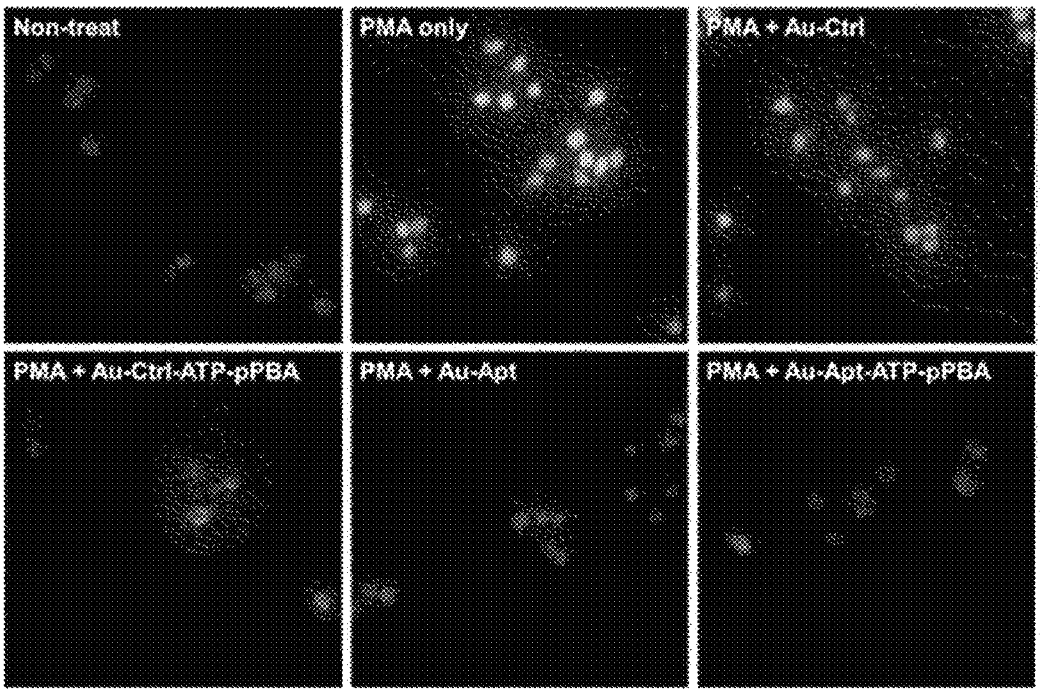
FIGS. 13(*a*) and 13(*b*) is a drawing showing the result of confirming the anti-inflammatory effects of Au-Apt, Au-Ctrl, Au-Apt-ATP-pPBA, and Au-Ctrl-ATP-pPBA according to an embodiment of the present disclosure on cells activated with PMA as fluorescence images of the intracellular reactive oxygen species.
Figure 13B:
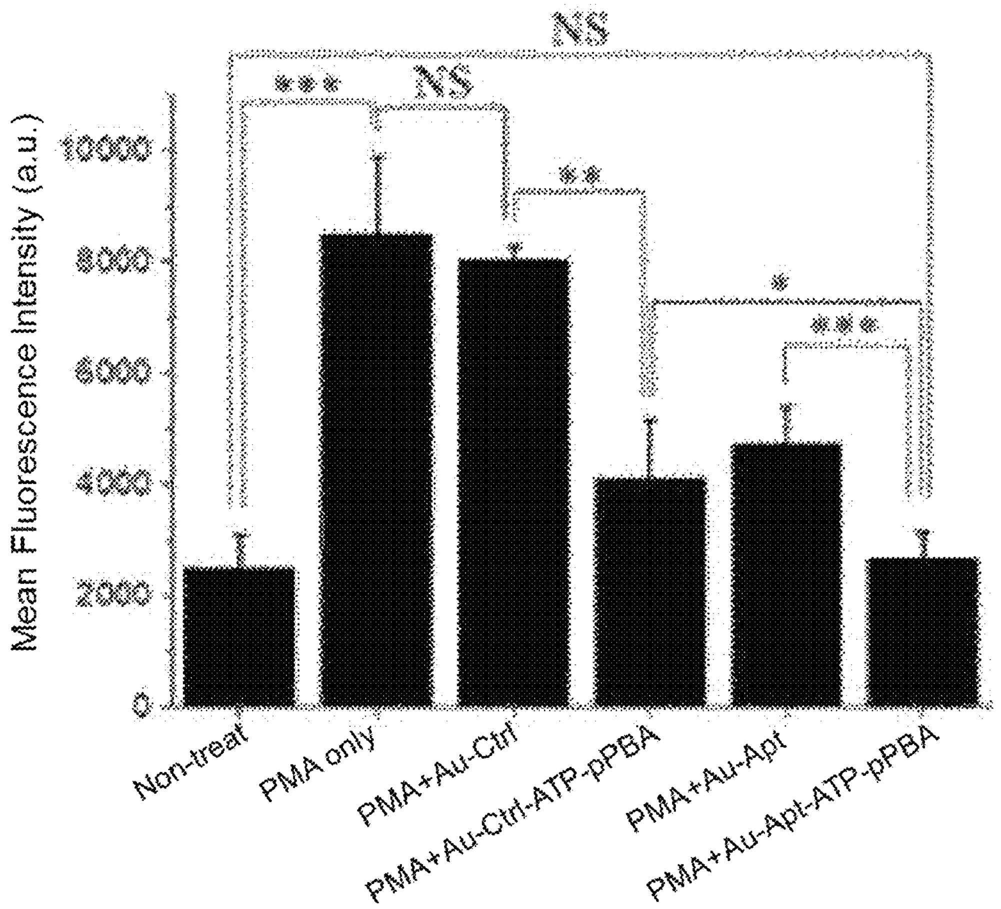

First, in the case of cells activated with PMA, the following experiment was carried out to confirm intracellular reactive oxygen species fluorescence. RAW 264.7 cells were seeded in a 12-well culture plate at 150,000 cells/well and cultured for 24 hours, and then the medium was replaced and 20 nM (based on gold nanoparticles) of Au-Apt, Au-Ctrl, Au-Apt-ATP-pPBA and Au-Ctrl-ATP-pPBA were treated with 200 ng/mL PMA. After 6 hours, the medium was removed, the cells were washed, treated with 20 μM 2', 7'-dichlorofluoresin diacetate, and 45 minutes later, intracellular reactive oxygen species fluorescence was observed under a fluorescence microscope. As a result, a significant reduction in reactive oxygen species was observed in Au-Ctrl-ATP-pPBA with reactive oxygen species scavenging capacity, and a decrease in reactive oxygen species through the interaction between reactive oxygen species-TNF-α was also observed in Au-Apt with TNF-α capturing ability. However, a significantly higher reduction in reactive oxygen species was observed in Au-Apt-ATP-pPBA with both reactive oxygen species scavenging capacity and TNF-α capturing ability compared to the two cases (FIG. 13).

In addition, in order to confirm whether reactive oxygen species, TNF-α, and an IL-6, which are secreted by inflammatory response and known as inflammatory factors, are regulated by the treatment of the polymer-coated gold nanoparticle-aptamer nanoconstructs of the present disclosure, RAW 264.7 cells were seeded in a 12-well culture plate at 200,000 cells/well and cultured for 24 hours, and then the medium was replaced and 20 nM (based on gold nanoparticles) of Au-Apt, Au-Ctrl, Au-Apt-ATP-pPBA and Au-Ctrl-ATP-pPBA were treated with 200 ng/mL PMA. After 24 hours, the medium was centrifuged at 13,200 rpm for 30 minutes, and then, the concentration of reactive oxygen species, TNF-α, and IL-6 in the supernatant was confirmed by Amplex red assay and enzyme immunoassay.

Figure 14A:
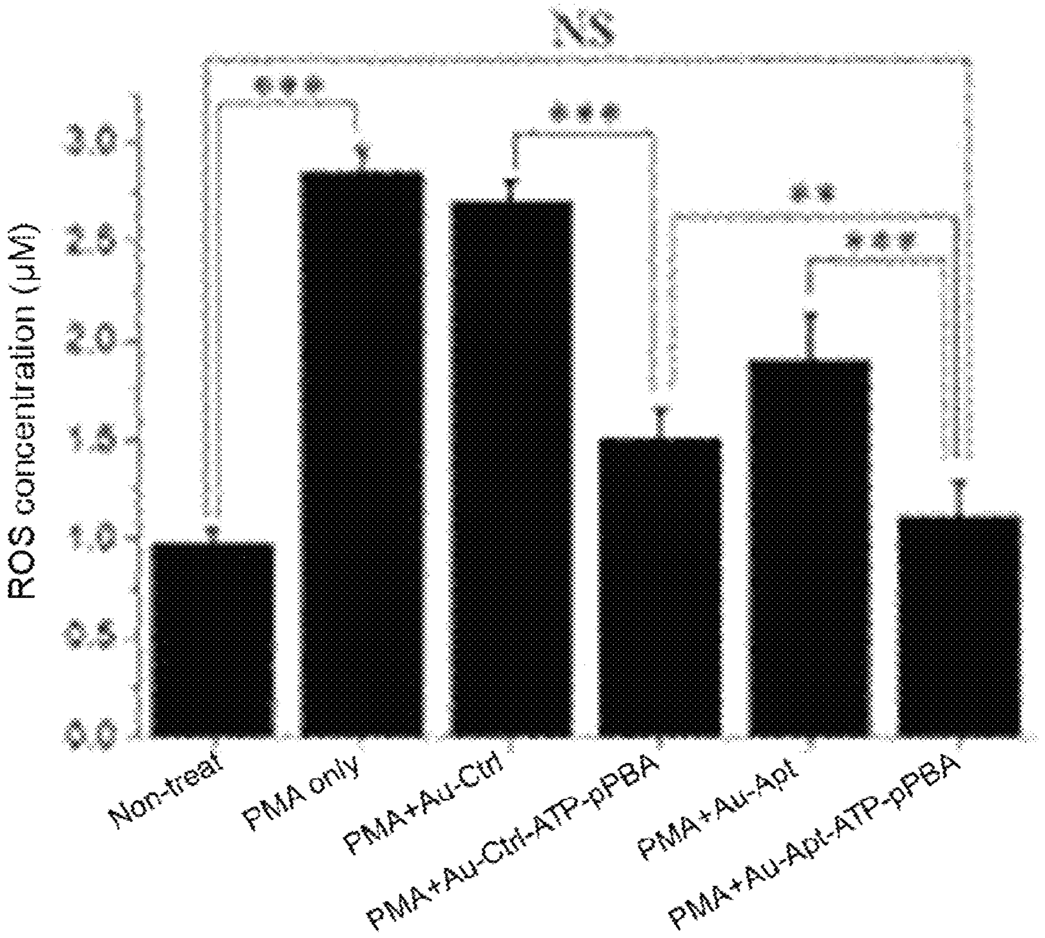
FIG. 14(*a*) through 14(*c*) is a drawing showing the result of confirming the anti-inflammatory effects of Au-Apt, Au-Ctrl, Au-Apt-ATP-pPBA, and Au-Ctrl-ATP-pPBA according to an embodiment of the present disclosure on cells activated with PMA as extracellular reactive oxygen species concentration, TNF-α concentration, and IL-6 concentration.
Figure 14B:
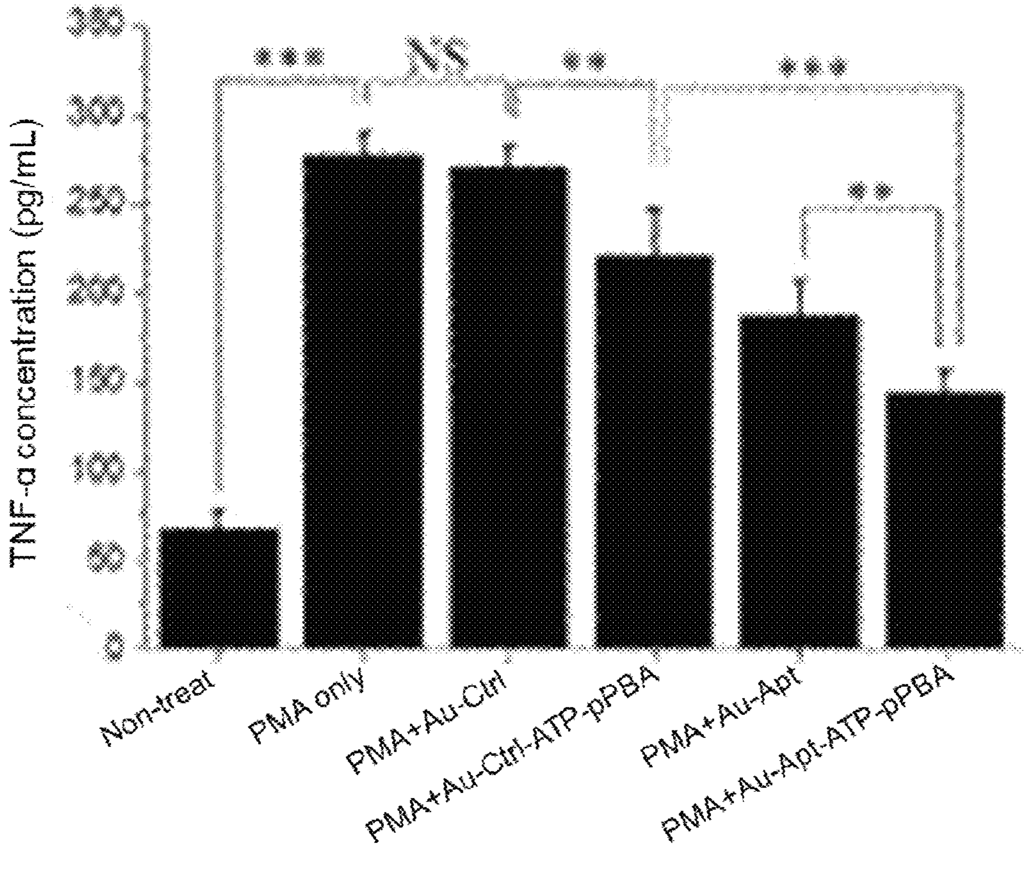
Figure 14C:
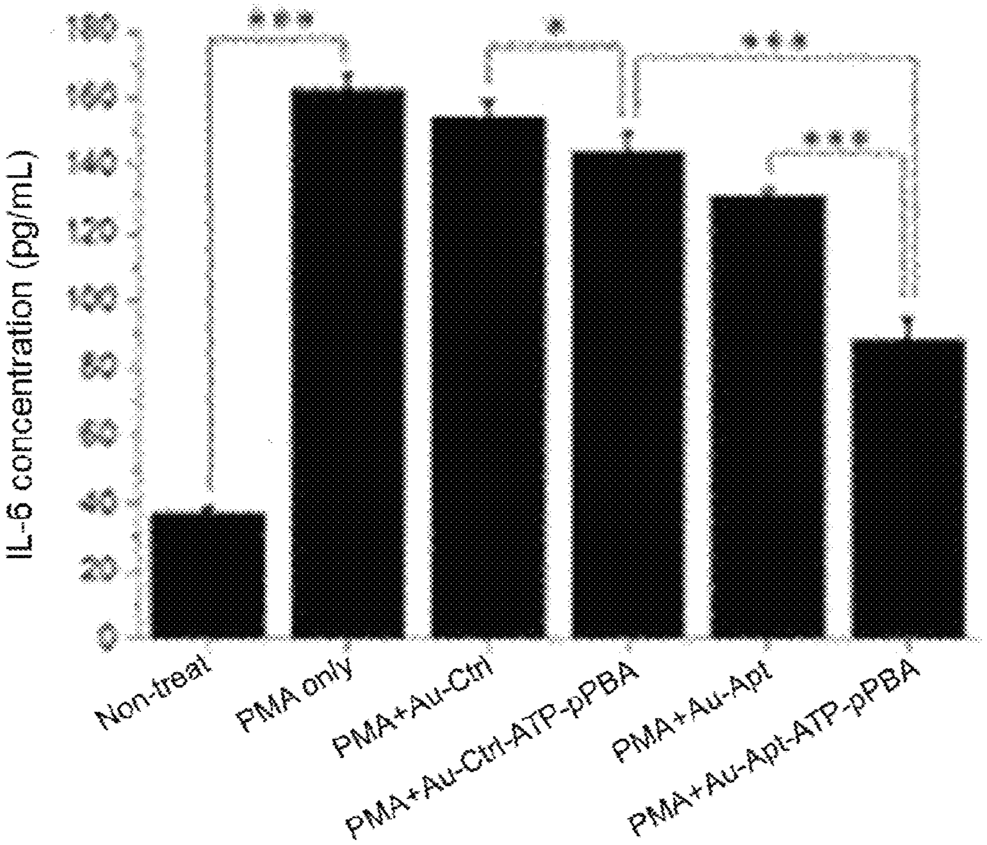

As a result, it was confirmed that Au-Ctrl-ATP-pPBA and Au-Apt reduced inflammation due to reactive oxygen species scavenging capacity and TNF-α capturing ability, respectively, and Au-Apt-ATP-pPBA with both abilities had a significantly superior anti-inflammatory effect (FIG. 14).

Figure 15A:
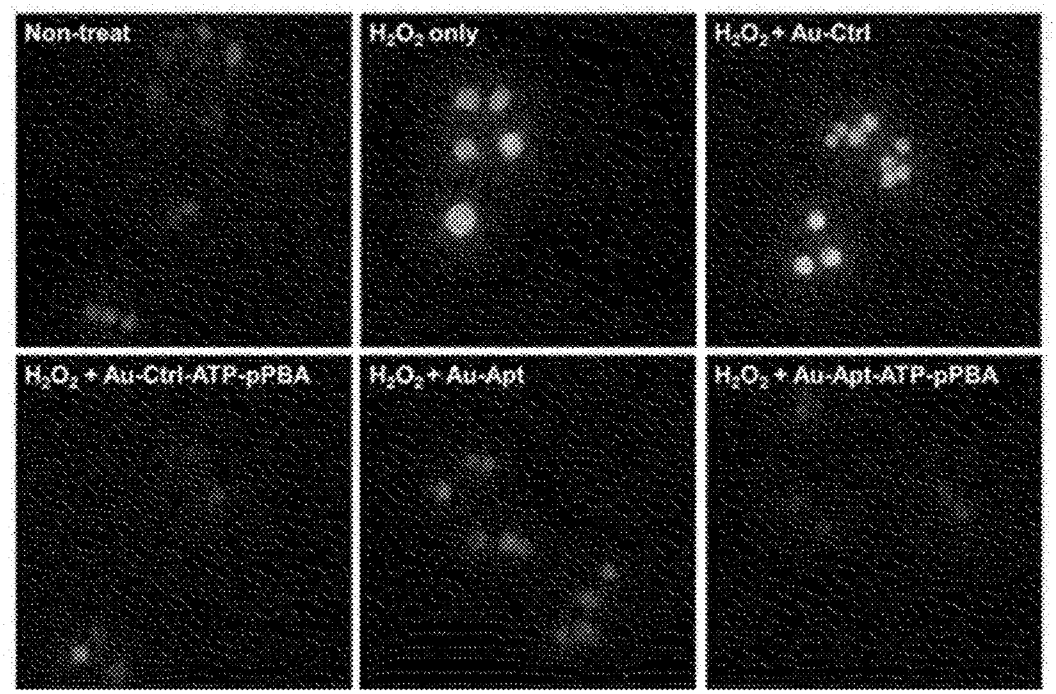
FIGS. 15(*a*) and 15(*b*) is a drawing showing the result of confirming the anti-inflammatory effects of Au-Apt, Au-Ctrl, Au-Apt-ATP-pPBA, and according Au-Ctrl-ATP-pPBA to an embodiment of the present disclosure on cells activated with hydrogen peroxide ($H_2O_2$) fluorescence images of the as intracellular reactive oxygen species.
Figure 15B:
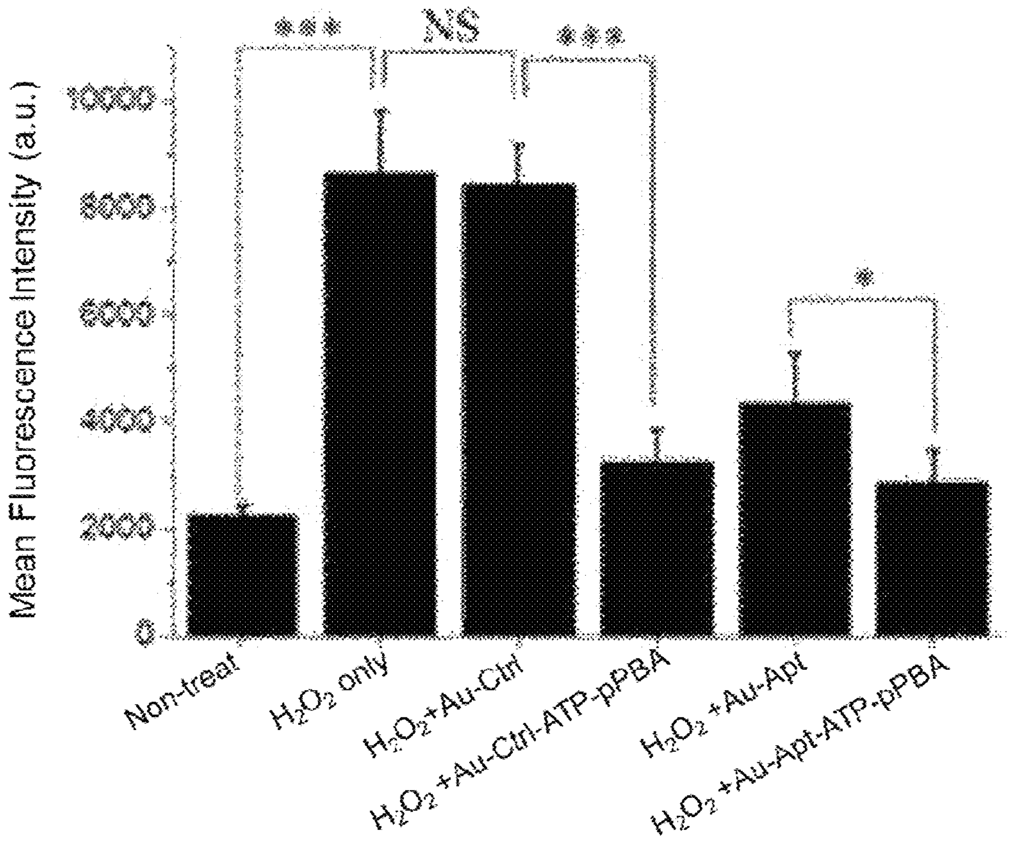
Figure 16A:
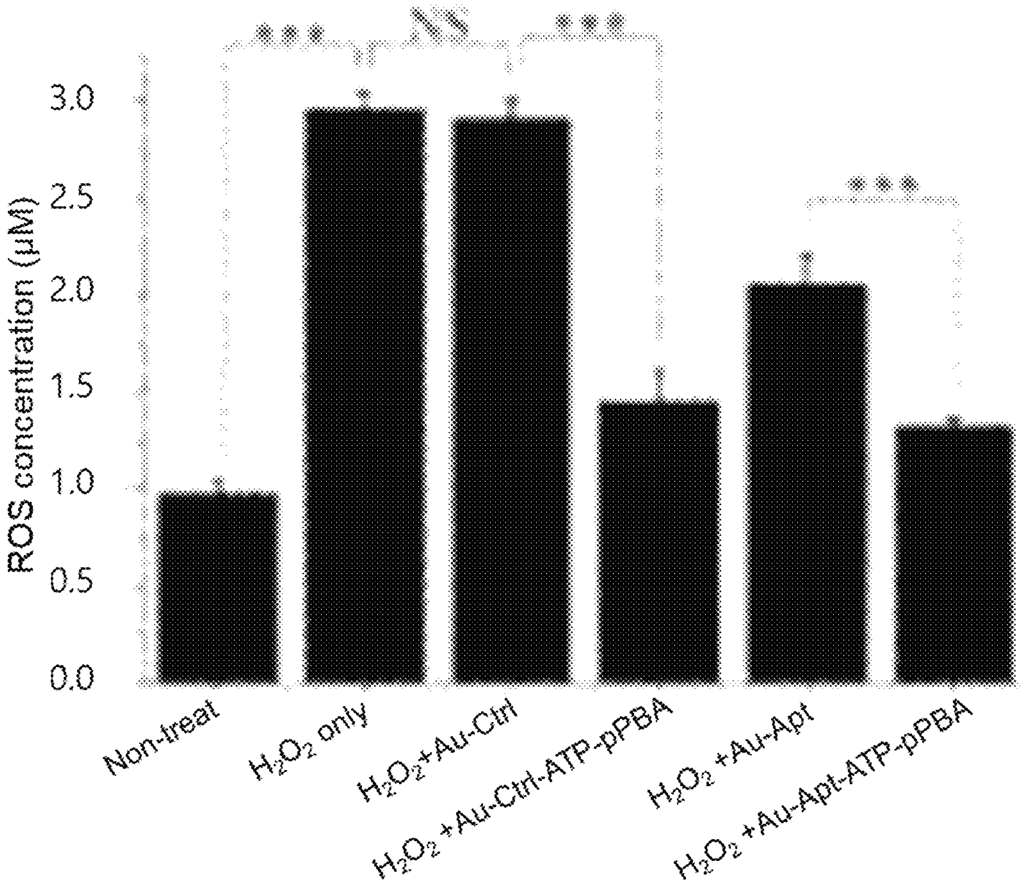
FIG. 16(*a*) through 16(*c*) is a drawing showing the result of confirming the anti-inflammatory effects of Au-Apt, Au-Ctrl, Au-Apt-ATP-pPBA, and Au-Ctrl-ATP-pPBA according to an embodiment of the present disclosure on cells activated with $H_2O_2$ as extracellular reactive oxygen species concentration, TNF-α concentration, and IL-6 concentration.
Figure 16B:
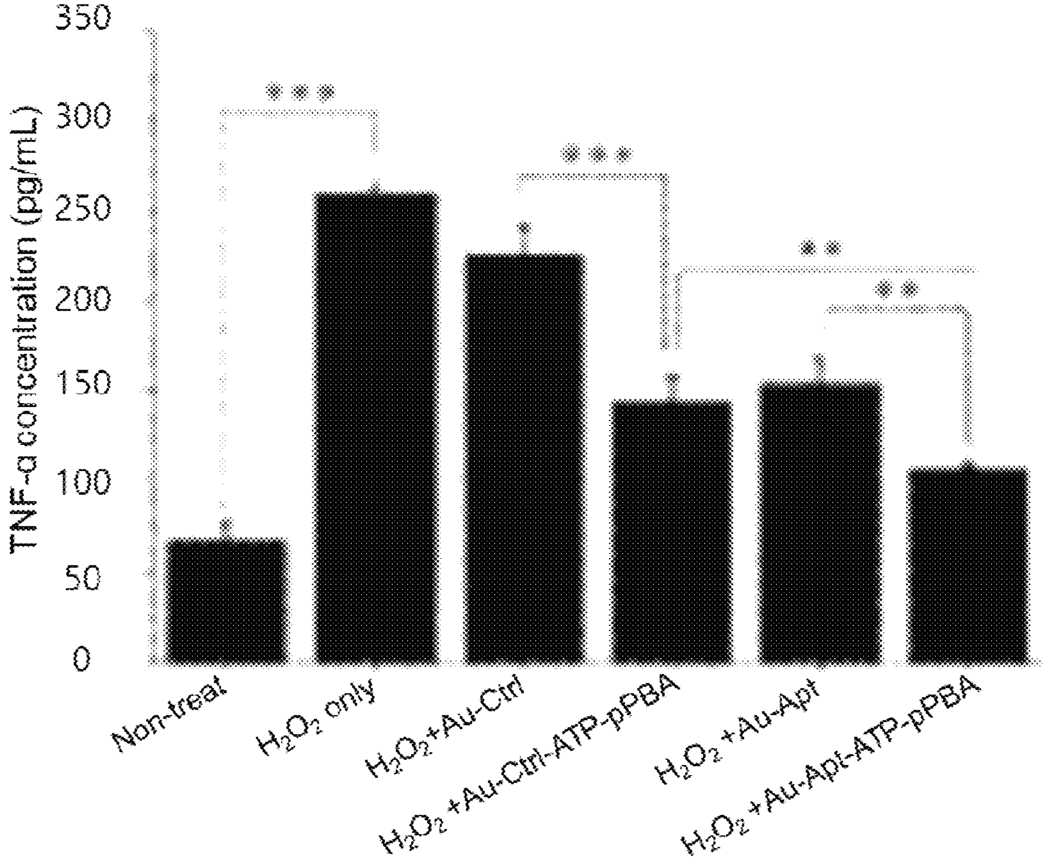
Figure 16C:
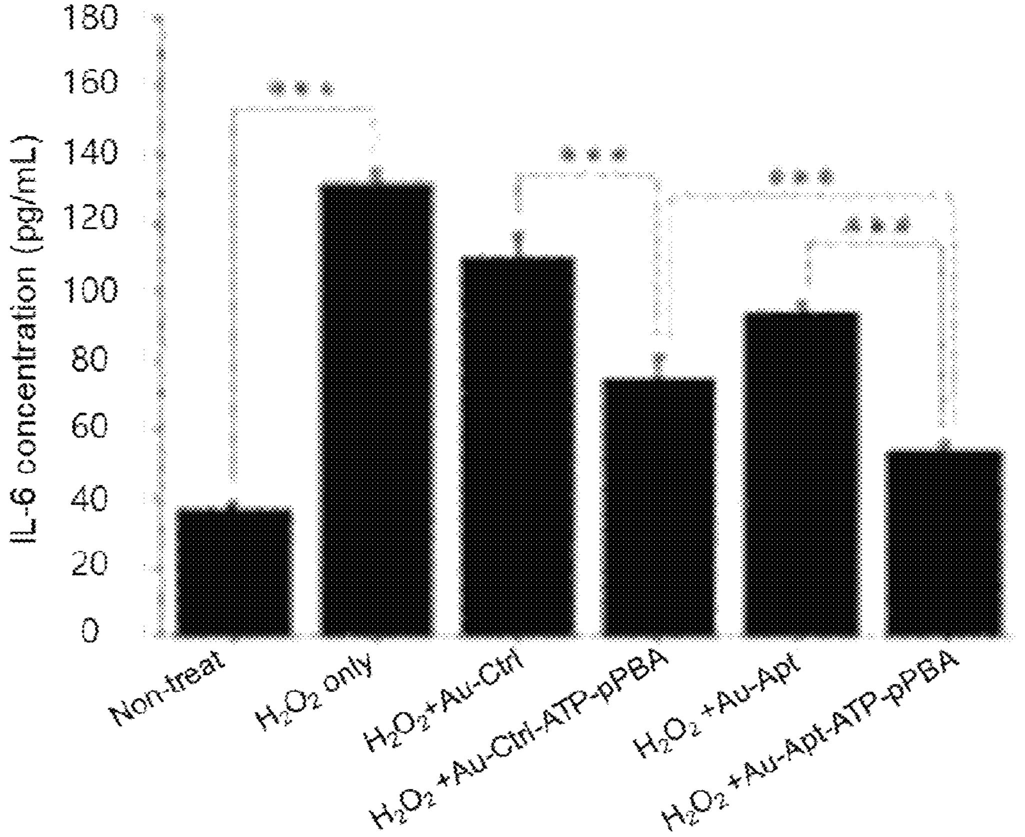

In the case of experiments on cells activated with $H_2O_2$, the same procedure as in the experimental method of cells activated with PMA was carried out except that 200 ng/ml PMA was changed to 100 μM $H_2O_2$, and a similar tendency was confirmed in the results (FIGS. 15 and 16).

Figure 17A:
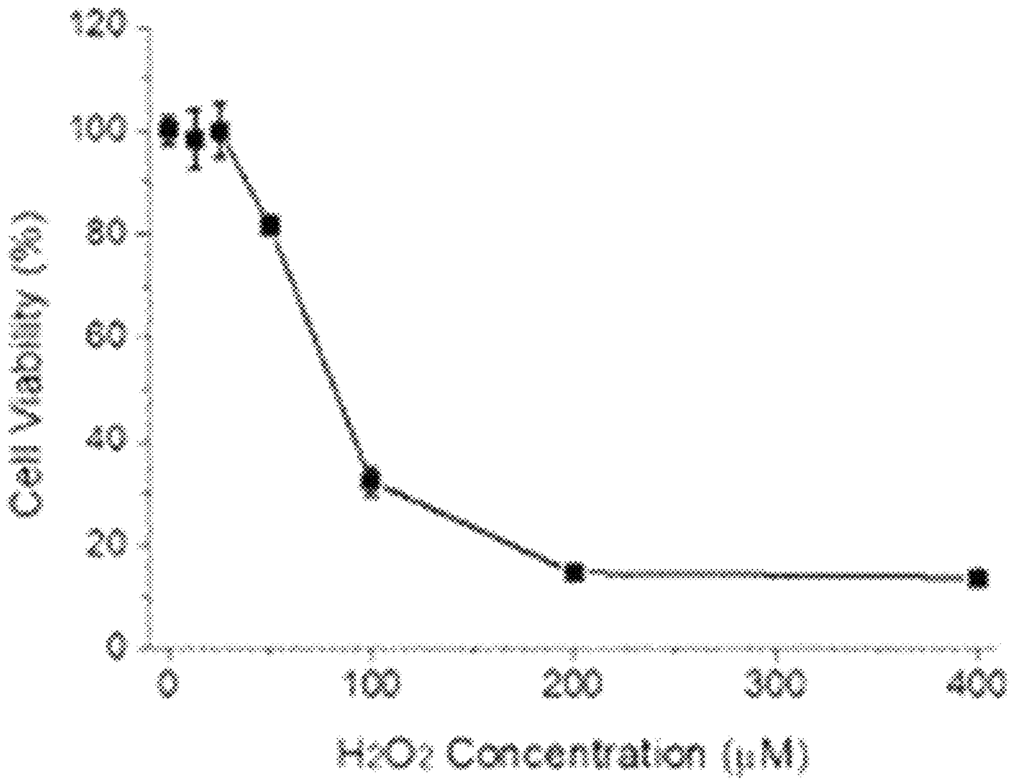
FIGS. 17(*a*) and 17(*b*) is a drawing showing the results of evaluating the cytotoxicity according to $H_2O_2$ concentration and the cytotoxicity when a sample comprising Au-Apt-ATP-pPBA according to an embodiment of the present disclosure is treated with $H_2O_2$.
Figure 17B:
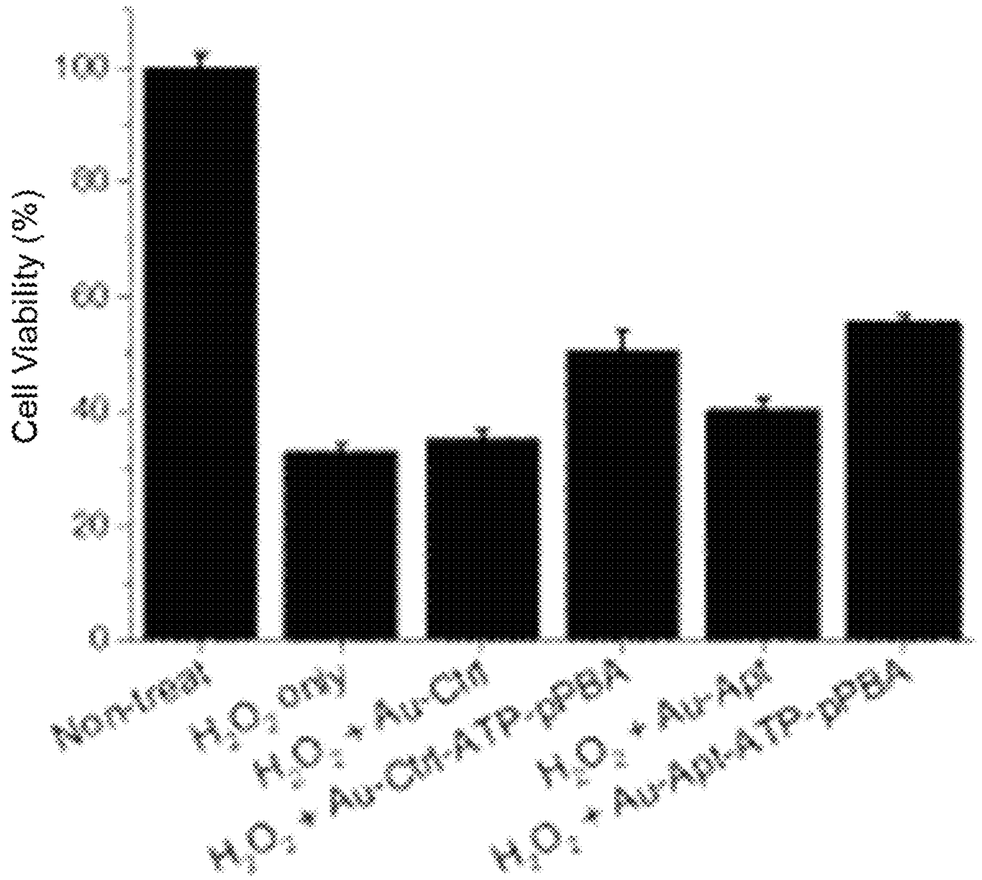

In addition, in order to confirm whether the cytotoxicity due to $H_2O_2$ is reduced by the anti-inflammatory effect, the concentration of $H_2O_2$ treatment was first determined to be 100 μM (FIG. 17 (*a*)).

RAW 264.7 cells were seeded in a 96-well culture plate at 10,000 cells/well, the medium was replaced after 24 hours, and 20 nM (based on gold nanoparticles) of Au-Apt, Au-Ctrl, Au-Apt-ATP-pPBA and Au-Ctrl-ATP-pPBA were treated with 100 μM $H_2O_2$. As a result of confirming the cell viability after 24 hours by the cytotoxicity and viability test method, it could be confirmed that the cell viability increased similarly to the anti-inflammatory effect shown for each sample (FIG. 17(*b*)).

Figure 18A:
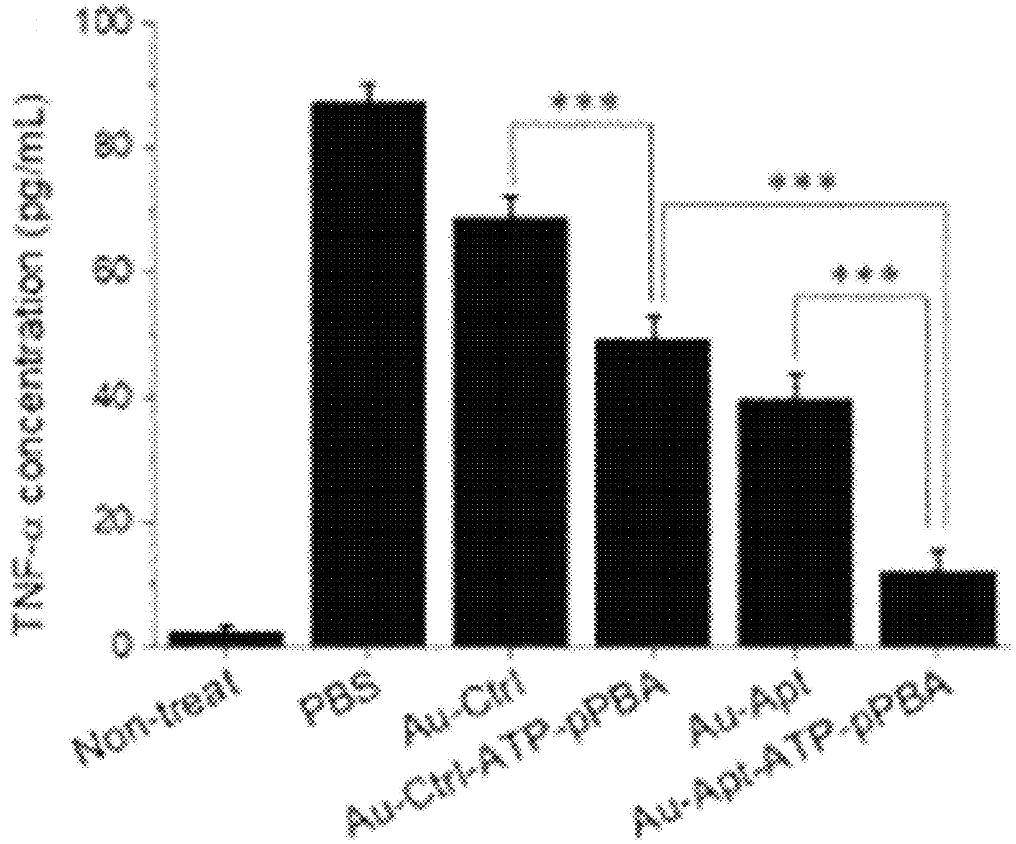
FIGS. 18(*a*) and 18(*b*) is a drawing showing the result of evaluating the anti-inflammatory effects of Au-Apt, Au-Ctrl, Au-Apt-ATP-pPBA, and Au-Ctrl-ATP-pPBA according to an embodiment of the present disclosure on the mouse peritonitis model as the concentration of TNF-α and IL-6 in the peritoneal fluid.
Figure 18B:
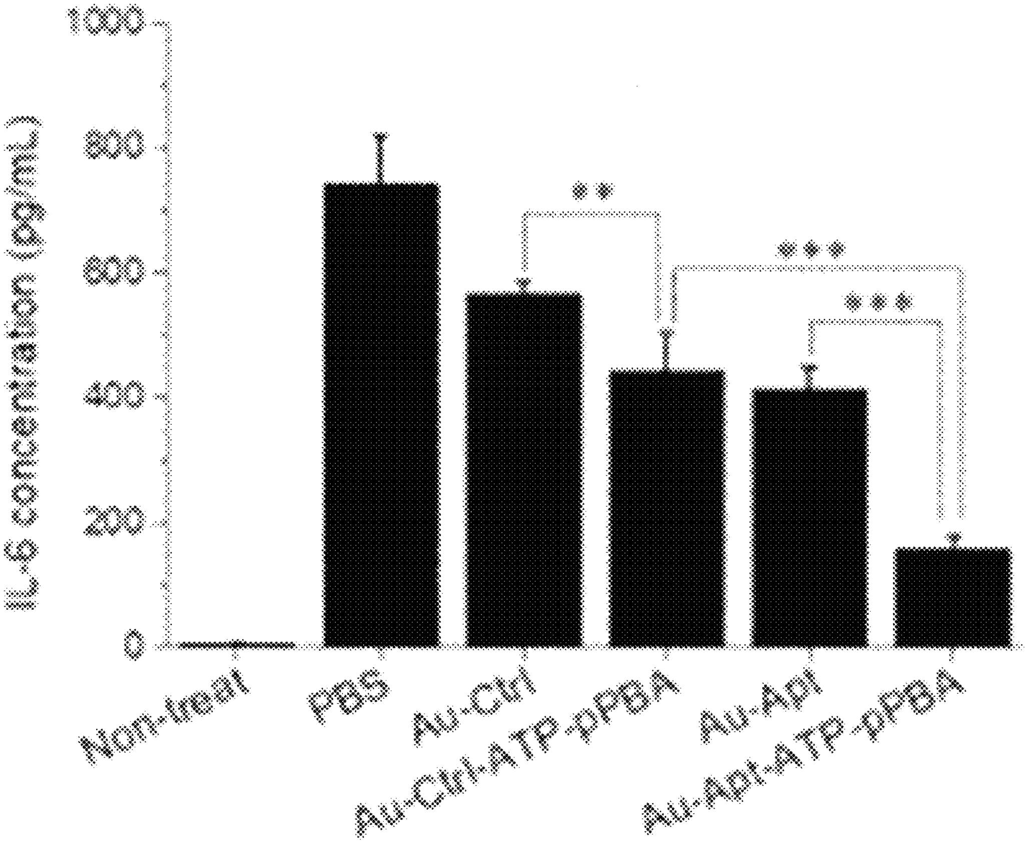
Figure 19A:
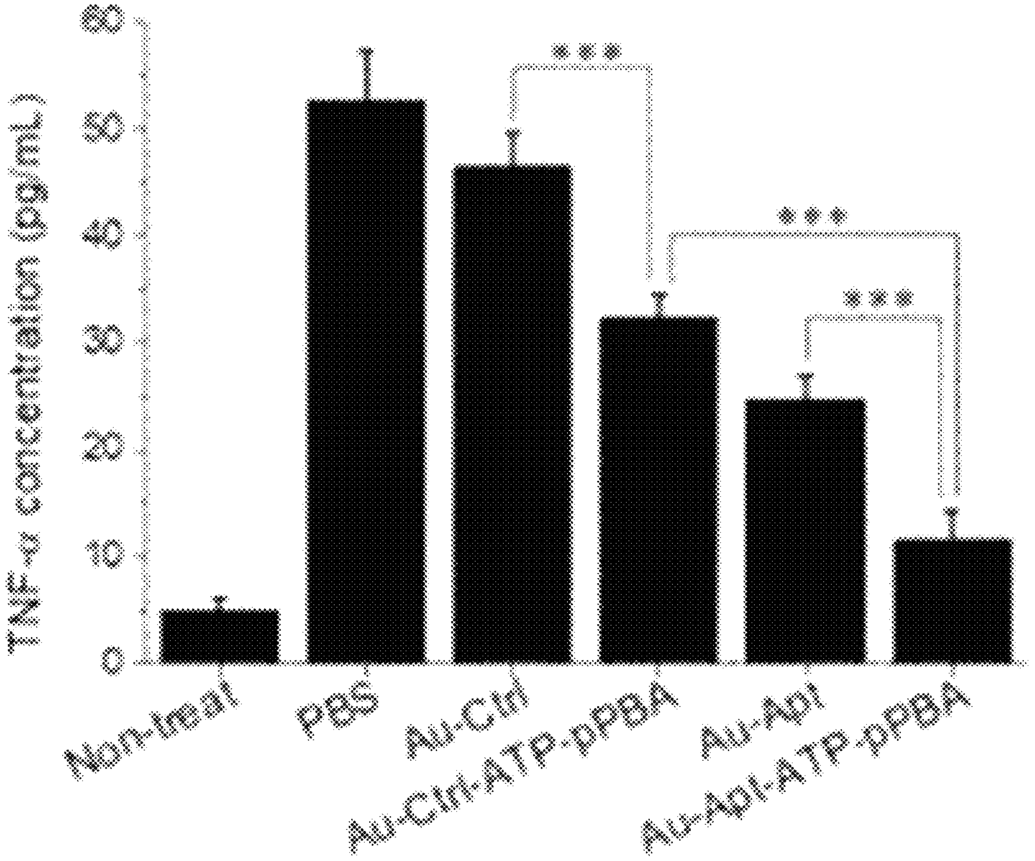
FIGS. 19(*a*) and 19(*b*) is a drawing showing the result of evaluating the anti-inflammatory effects of Au-Apt, Au-Ctrl, Au-Apt-ATP-pPBA, and according Au-Ctrl-ATP-pPBA to an embodiment of the present disclosure on the mouse peritonitis model as the concentration of TNF-α and IL-6 in the blood.
Figure 19B:
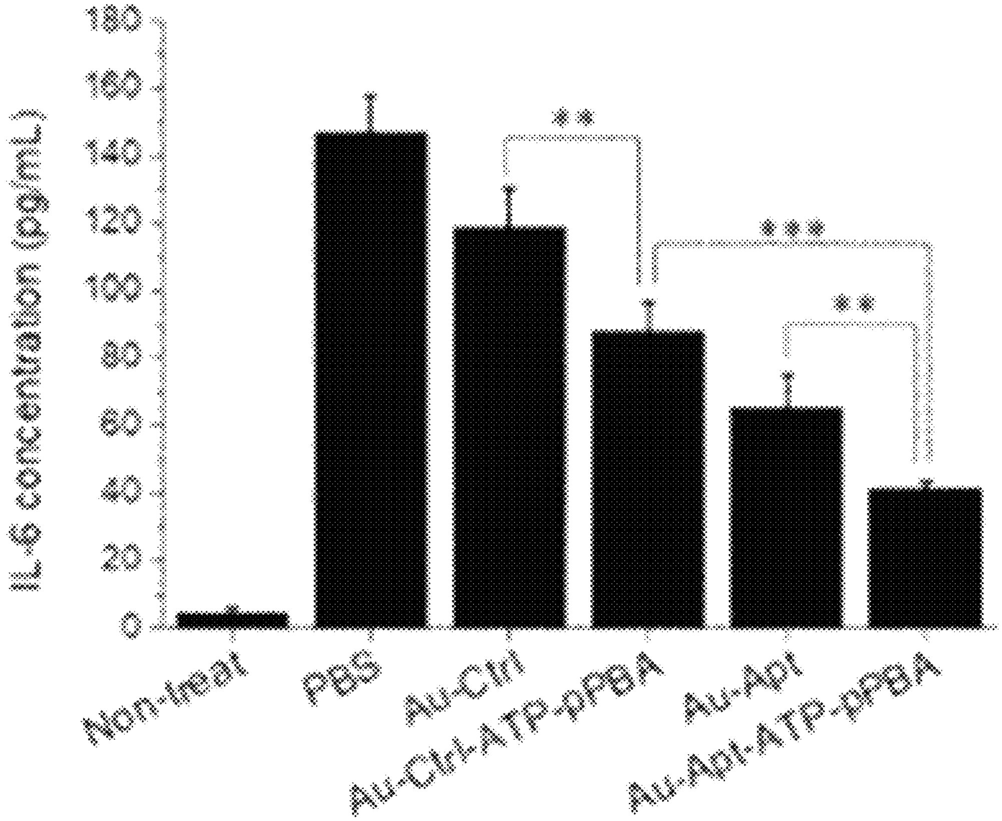

Example 2-3. Confirmation of Anti-Inflammatory Effect of Polymer-Coated Gold Nanoparticle-Aptamer Nanoconstructs in the Mice In order to confirm the anti-inflammatory effect of polymer-coated gold nanoparticle-aptamer nanoconstructs (Au-Apt-ATP-pPBA, Au-Ctrl-ATP-pPBA) in the mice, 800 μl of 1 mg/ml zymosan was injected into the abdominal cavity of the mice to create peritonitis. After 1 hour, 200 μl of 100 nM (based on gold nanoparticles) of Au-Apt, Au-Ctrl, Au-Apt-ATP-pPBA and Au-Ctrl-ATP-pPBA were intraperitoneally injected, and after an additional 5 hours, peritoneal washing was carried out on the mice to collect peritoneal fluid, and whole blood was collected through cardiac blood collection. TNF-α concentration and IL-6 concentration in peritoneal fluid and whole blood were confirmed by enzyme immunoassay. As a result, it was confirmed that with a tendency similar to the results in cells, Au-Ctrl-ATP-pPBA and Au-Apt reduced inflammation due to reactive oxygen species scavenging capacity and TNF-α capturing ability, respectively, and Au-Apt-ATP-pPBA with both abilities had a significantly superior anti-inflammatory effect (FIGS. 18 and 19).

The invention claimed is:

1. A nanoconstruct consisting of:

a gold nanoparticle;

an aptamer with which the surface of the gold nanoparticle is modified; and polymerized phenylboronic acid coated on the aptamer through ATP as a mediator, wherein the aptamer has a sequence of SEQ ID NO: 1 or 2.

2. The nanoconstruct according to claim 1, wherein the gold nanoparticle has a size of 10-200 nm.

3. The nanoconstruct according to claim 1, wherein the aptamer has a single-stranded DNA sequence simultaneously having an aptamer for a disease-related factor and an aptamer for ATP.

4. The nanoconstruct according to claim 3, wherein the disease-related factor is one selected from TNF-α, VEGF, IL-6, IL-1, MCP-1, and thrombin.

5. The nanoconstruct according to claim 4, wherein the disease-related factor is one selected from TNF-α and VEGF.

6. The nanoconstruct according to claim 5, wherein the disease-related factor is TNF-α.

7. The nanoconstruct according to claim 5, wherein the disease-related factor is VEGF.

8. The nanoconstruct according to claim 1, wherein the aptamer has a sequence of SEQ ID NO: 1.

9. The nanoconstruct according to claim 1, wherein the aptamer has a sequence of SEQ ID NO: 2.

10. The nanoconstruct according to claim 1, wherein the polymerized phenylboronic acid is a hydrophilic polymer comprising phenylboronic acid.

11. An anti-inflammatory therapeutic agent comprising the nanoconstruct according to claim 1 as an active ingredient.

12. An anticancer therapeutic agent comprising the nanoconstruct according to claim 1 as an active ingredient.

13. A therapeutic agent for macular degeneration, comprising the nanoconstruct according to claim 1 as an active ingredient.

* * * * *